US008162883B2

(12) United States Patent
Takemoto

(10) Patent No.: US 8,162,883 B2
(45) Date of Patent: Apr. 24, 2012

(54) PUNCTURE NEEDLE ASSEMBLY AND MEDICINAL LIQUID INJECTOR

(75) Inventor: Masafumi Takemoto, Nakakoma-gun (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 0 days.

(21) Appl. No.: 12/891,156

(22) Filed: Sep. 27, 2010

(65) Prior Publication Data
US 2011/0077592 A1    Mar. 31, 2011

Related U.S. Application Data

(63) Continuation of application No. PCT/JP2009/056187, filed on Mar. 26, 2009.

(30) Foreign Application Priority Data

Mar. 28, 2008  (JP) .................................. 2008-088634

(51) Int. Cl.
  *A61M 5/00*   (2006.01)
(52) U.S. Cl. ...................................................... 604/111
(58) Field of Classification Search .................. 604/110, 604/111, 192, 198
  See application file for complete search history.

(56) References Cited

U.S. PATENT DOCUMENTS

| | | | |
|---|---|---|---|
| 4,737,144 A * | 4/1988 | Choksi ........................... | 604/198 |
| 4,894,055 A | 1/1990 | Sudnak | |
| 5,104,384 A | 4/1992 | Parry | |
| 5,176,643 A * | 1/1993 | Kramer et al. ................. | 604/135 |
| 5,242,401 A * | 9/1993 | Colsky ........................... | 604/110 |
| 5,295,975 A * | 3/1994 | Lockwood, Jr. ............... | 604/198 |
| 5,429,612 A | 7/1995 | Berthier | |
| 5,451,210 A * | 9/1995 | Kramer et al. ................. | 604/137 |
| 5,688,241 A * | 11/1997 | Asbaghi ......................... | 604/110 |
| 5,873,856 A * | 2/1999 | Hjertman et al. .............. | 604/117 |

(Continued)

FOREIGN PATENT DOCUMENTS

JP          6-502787 A         3/1994

(Continued)

OTHER PUBLICATIONS

International Search Report (PCT/ISA/210) issued on Apr. 21, 2009, by Japanese Patent Office as the International Searching Authority for International Application No. PCT/JP2009/056187.

(Continued)

*Primary Examiner* — Nicholas Lucchesi
*Assistant Examiner* — Aarti B Berdichevsky
(74) *Attorney, Agent, or Firm* — Buchanan Ingersoll & Rooney PC

(57) ABSTRACT

A puncture needle assembly has a needle tube, a protector capable of moving between a first position at which the protector covers the tip of the needle tube and a second position at which the tip is exposed, a body for movably supporting the protector and having an elastic deformable section, and an engagement preventing member removably mounted to the base end of a protector body. The protector has a rib. A portion on the head end side of the rib forms a contact section, and a portion on the base end side of the rib forms an engaging section engaging with the elastic deformable section. When the protector moves from the first position to the second position, the engagement preventing member moves together with the protector to prevent the engaging section from engaging with the elastic deformable section and elastically deforms the elastic deformable section.

31 Claims, 16 Drawing Sheets

U.S. PATENT DOCUMENTS

| | | | |
|---|---|---|---|
| 6,159,184 A * | 12/2000 | Perez et al. | 604/192 |
| 6,648,856 B1 * | 11/2003 | Argento | 604/192 |
| 6,855,129 B2 * | 2/2005 | Jensen et al. | 604/110 |
| 7,314,464 B2 * | 1/2008 | Giambattista et al. | 604/198 |
| 7,553,293 B2 * | 6/2009 | Jensen et al. | 604/110 |
| 2002/0045864 A1 * | 4/2002 | Perez et al. | 604/198 |
| 2003/0139705 A1 * | 7/2003 | Larsen et al. | 604/198 |
| 2005/0171485 A1 * | 8/2005 | Larsen et al. | 604/198 |
| 2008/0312590 A1 | 12/2008 | Barrow-Williams et al. | |
| 2009/0124971 A1 * | 5/2009 | Shue et al. | 604/110 |
| 2009/0221972 A1 | 9/2009 | Gratwohl et al. | |
| 2009/0259196 A1 | 10/2009 | Gratwohl et al. | |

FOREIGN PATENT DOCUMENTS

| | | |
|---|---|---|
| JP | 2872318 B2 | 3/1999 |
| JP | 2008-500858 A | 1/2008 |
| WO | 2008/028304 A1 | 3/2008 |
| WO | 2008/028312 A1 | 3/2008 |

OTHER PUBLICATIONS

Written Opinion (PCT/ISA/237) issued on Apr. 21, 2009, by Japanese Patent Office as the International Searching Authority for International Application No. PCT/JP2009/056187.

* cited by examiner

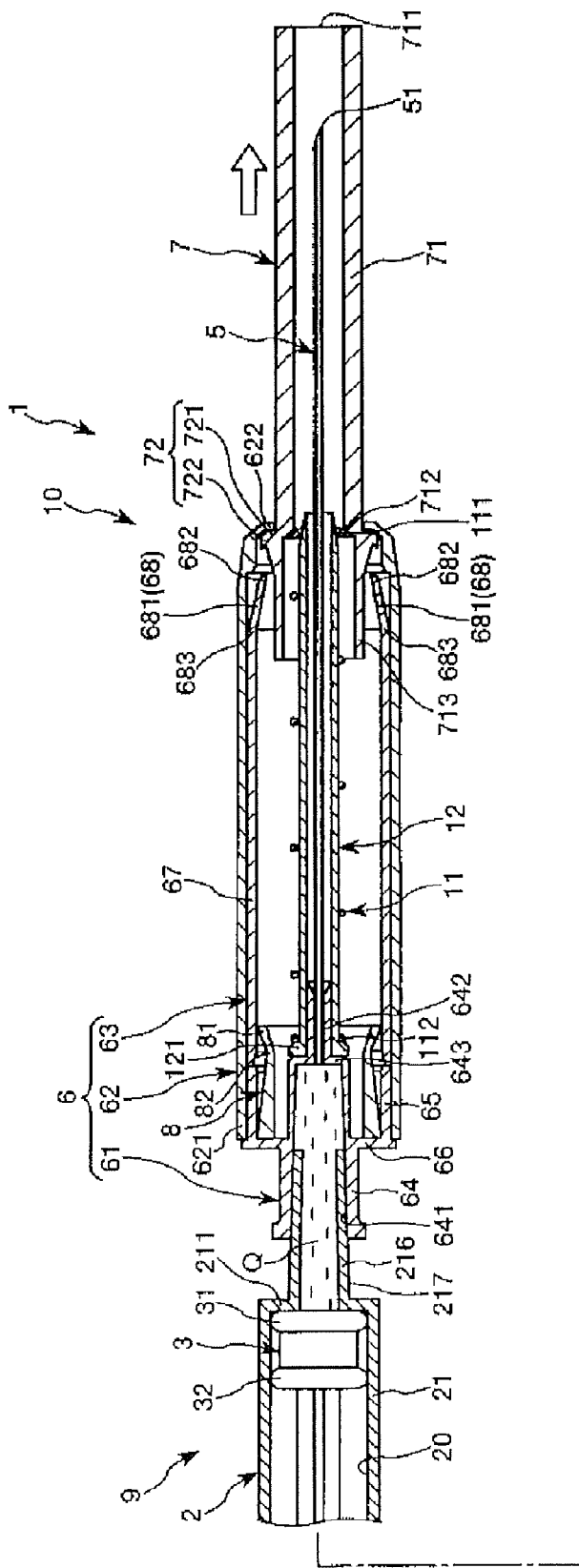
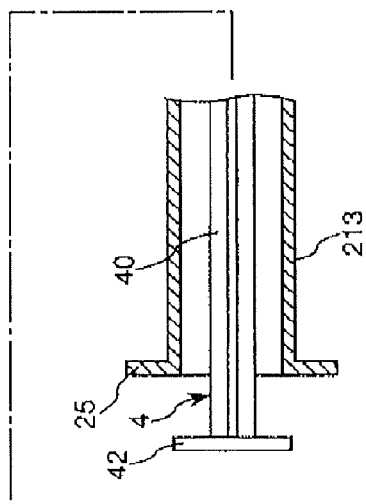
FIG. 5

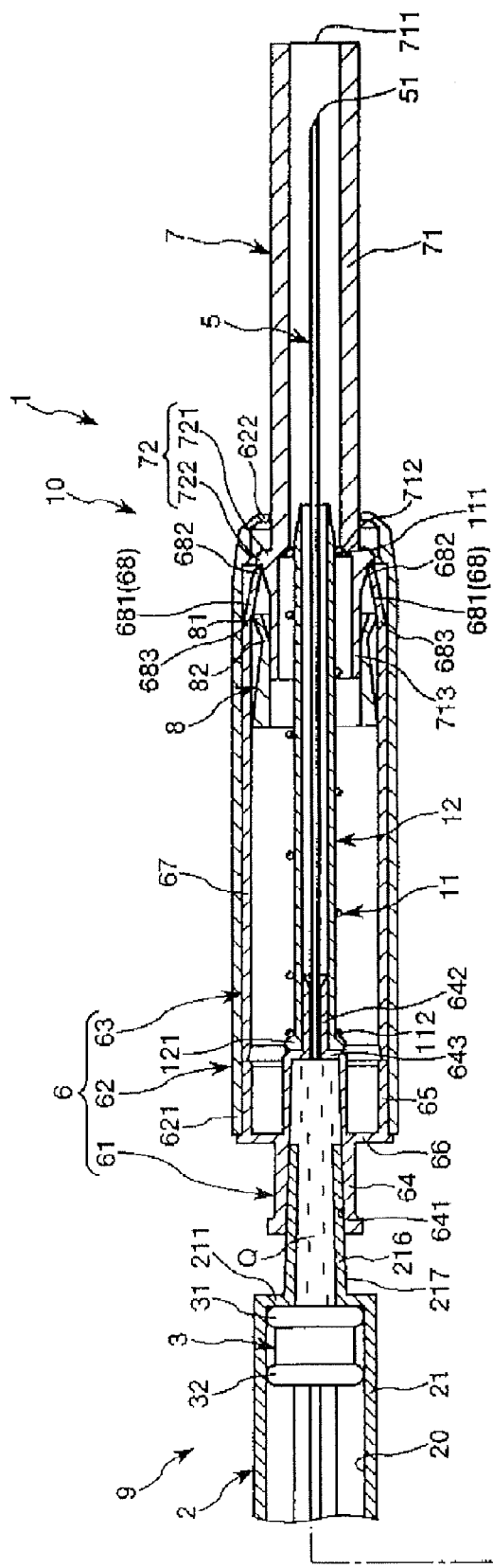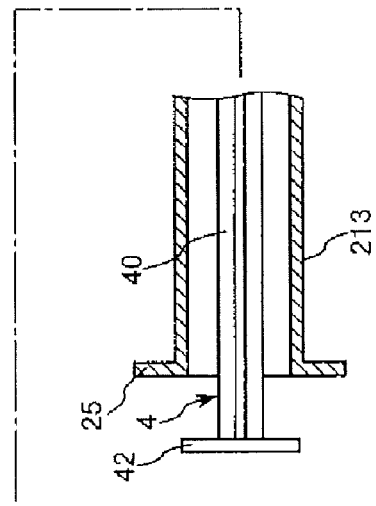
FIG. 7

PUNCTURE NEEDLE ASSEMBLY AND MEDICINAL LIQUID INJECTOR

TECHNICAL FIELD

The present invention relates to a puncture needle assembly and a medicinal liquid injector provided with the same.

BACKGROUND ART

Prefilled syringes, each of which is preliminarily filled with a medicinal liquid, have been known. Such prefilled syringes each include an outer tube provided with a discharge port at its distal end, a gasket inserted into the outer tube, and a plunger connected to the gasket. The medicinal liquid is enclosed in a space surrounded by the outer tube and the gasket.

In the case of injecting a medicinal liquid, for example, into a living body by use of the prefilled syringe, a needle assembly having a hollow needle is mounted on the discharge port of the outer tube, whereby the prefilled syringe is used in such a mounted condition (see, for example, Patent Document 1). Further, in the mounted condition, the inside of the outer tube communicates with the inside of the hollow needle. The needle assembly (protective sleeve) described in Patent Document 1 includes a hollow needle, a tubular outside member (outside sleeve member) disposed on an outer peripheral side of the hollow needle and supporting and fixing a base end portion of the hollow needle, a tubular inside member (inside sleeve member) disposed between the outside member and the hollow needle, the tubular inside member being coaxial with the outside member and movable along the axial direction of the outside member, and a coil spring for biasing the inside member toward a distal end side (in the distal direction). In the needle assembly having such a configuration, by being moved relative to the outside member in the axial direction thereof, the inside member can assume a first state in which a needle body inclusive of a needle point is covered, and a second state in which the needle point is exposed. In addition, under a biasing force of the coil spring, the inside member can be maintained in the first state.

In the needle assembly described in Patent Document 1, however, if only the inside member in the first state is pushed toward the base end side (in the proximal direction) against the biasing force of the coil spring, the inside member is capable of being brought into the second state, even after the needle assembly has been used once. Therefore, in the case that such a pushing force is unintentionally exerted on the inside member, the inside member is brought into the second state, leading to the possibility that a finger or the like may mistakenly be pierced by the needle point, which is exposed from the inside member.

Patent Document 1: Japanese Patent No. 2872318

DISCLOSURE OF THE INVENTION

It is an object of the present invention to provide a puncture needle assembly and a medicinal liquid injector, configured such that unintentional exposure of the needle point of a needle tube from a protector can reliably be prevented.

In order to achieve the above object, the present invention is characterized by a puncture needle assembly including:

a needle tube having a sharp needle point at a distal end thereof;

a body including a tubular body section in which the needle tube is partially inserted, a hub to which a base end portion of the needle tube is fixed and which is provided at a base end portion of the tubular body section, and an elastic deformable section provided on a distal end side relative to the base end portion of the tubular body section;

a protector supported on the body so as to be capable of moving along an axial direction of the needle tube between a first position at which the protector covers at least the needle point of the needle tube and a second position at which the needle point is exposed and which is on a base end side relative to the first position, the protector having an engaging section engaging with the elastic deformable section when the protector is in the first position;

an engagement preventing member which, when the protector moves from the first position to the second position, makes contact with the engaging section to exhibit an engagement preventing function, and which permits the engaging section to move past the elastic deformable section without engaging with the elastic deformable section; and biasing means biasing the protector in a direction from the second position toward the first position, wherein the protector is biased by a biasing force of the biasing means to move to the first position when the protector is pushed to move from the first position to the second position against the biasing force of the biasing means and then pushing thereof is released, and thereafter, when it is attempted to move the protector in the first position toward the second position, the engagement preventing function of the engagement preventing member is not exhibited and the engaging section engages with the elastic deformable section, thereby preventing the protector from moving toward the side of the second position.

According to the present invention, as indicated above, even if it is attempted to further move the protector, which has been moved from the first position to the second position and then returned again to the first position, to the second position, movement of the protector is restrained.

More specifically, since the engaging section of the protector engages with the elastic deformable section, movement of the protector toward the side of the second position is inhibited. This ensures that unintentional exposure (protrusion) of the needle point of the needle tube from the protector can reliably be prevented, and therefore, mistaken puncturing with the needle point can securely be prevented from occurring.

In addition, according to the present invention, the elastic deformable section is elastically deformed under pressure by the engagement preventing member when the protector moves from the first position to the second position. In other words, until the protector is moved (while the puncture needle assembly is in an unused state), the elastic deformable section is in a natural state with no external forces exerted thereon. This ensures that even when the puncture needle assembly is stored for a long time, for example, the elastic deformable section is securely prevented from developing an unintended semi-permanent deformation therein. Therefore, the shape of the elastic deformable section is maintained, and the elastic deformable section can be elastically deformed in a preferable manner. Consequently, when the engaging section of the protector comes into engagement with the elastic deformable section, as mentioned above, engagement is carried out reliably therebetween.

Further, in the puncture needle assembly according to the present invention, preferably, the engagement preventing member is mounted on the protector, and when the protector moves from the first position to the second position, the engagement preventing member moves together with the protector so as to move past the elastic deformable section.

This ensures that when the protector moves from the first position to the second position, the engaging section of the protector can move past a distal portion of the elastic deformable section without coming into engagement with the elastic deformable section.

In addition, in the puncture needle assembly according to the present invention, preferably, the protector is tubular in overall shape, and the engaging section is composed of a projecting section formed at an outer peripheral portion of the protector, and the engagement preventing member is tubular in overall shape and is mounted on an outer peripheral portion on the base end side of the engaging section of the protector.

This ensures that when the protector moves from the first position to the second position, the engagement preventing member can move assuredly together with the protector and thereby exhibit an engagement preventing function (i.e., the protector can move together with the engagement preventing member).

Further, in the puncture needle assembly according to the present invention, preferably, a gap is formed between an inner peripheral surface of the engagement preventing member and an outer peripheral surface of the protector, in a condition where the engagement preventing member is mounted on the protector.

This ensures that when the engagement preventing member becomes released (separated) from the protector, or in other words, when the protector moves from the second position to the first position, the engagement preventing member can be released smoothly and assuredly.

In addition, in the puncture needle assembly according to the present invention, preferably, the outside diameter of a distal portion of the engagement preventing member gradually increases from the base end side toward the distal end side.

This ensures that when the protector moves from the first position to the second position, the elastic deformable section can be elastically deformed in a smooth manner.

Further, in the puncture needle assembly according to the present invention, preferably, the engaging section is composed of a projecting section formed at an outer peripheral portion of the protector along the circumferential direction.

This ensures that the projecting section can engage reliably with the elastic deformable section.

In addition, in the puncture needle assembly according to the present invention, preferably, the outside diameter of the distal end of the engagement preventing member is not less than an outside diameter at the engaging section of the protector.

This ensures that when the protector moves from the first position to the second position, the engaging section can securely be prevented from coming into engagement with the elastic deformable section, and the elastic deformable section can be elastically deformed so that the engaging section can move past the elastically deformable section.

Further, in the puncture needle assembly according to the present invention, preferably, when the protector is in the first position, the elastic deformable section is located on an outer peripheral side of the engagement preventing member, in a condition where the engagement preventing member is mounted on the protector, and when the protector moves from the first position to the second position, the engagement preventing member is capable of moving together with the protector and pressing the elastic deformable section outwardly so as to elastically deform the elastic deformable section.

This ensures that when the protector moves from the first position to the second position, the engaging section of the protector can move past the distal portion of the elastic deformable section without coming into engagement with the elastic deformable section.

In addition, in the puncture needle assembly according to the present invention, preferably, when the protector is in the first position, a distal portion of the elastic deformable section is located at an intermediate portion of the engagement preventing member, in a condition where the engagement preventing member is mounted on the protector.

This ensures that when the protector moves from the first position to the second position, the engaging section of the protector can move past the distal portion of the elastic deformable section without coming into engagement with the elastic deformable section.

Further, in the puncture needle assembly according to the present invention, preferably, the engagement preventing member is mounted on the protector upon return of the protector from the second position to the first position.

This ensures that when the protector returns by moving from the second position to the first position, such movement is performed stably.

In addition, the puncture needle assembly according to the present invention preferably includes a release preventing means for preventing the engagement preventing member from becoming released from the protector when the protector moves from the second position to the first position.

This ensures that when the protector returns by moving from the second position to the first position, such movement is performed stably.

Further, the puncture needle assembly according to the present invention preferably includes an assisting means for assisting assured release of a contact state of the engagement preventing member with the engaging section when the protector moves from the second position to the first position.

This ensures that when the protector moves from the second position to the first position, contact between the engagement preventing member and the engaging section can be released assuredly.

In addition, in the puncture needle assembly according to the present invention, preferably, the engagement preventing member becomes released from the protector when the protector moves from the second position to the first position.

This ensures that when the protector in the first position is about to be moved again to the second position, the engagement preventing function of the engagement preventing member is not exhibited and the engaging section comes into engagement with the elastic deformable section, whereby the protector can securely be inhibited from moving toward the side of the second position.

Further, in the puncture needle assembly according to the present invention, preferably, when the protector moves from the second position to the first position, a contact state of the engagement preventing member with the engaging section becomes released, so that the engagement preventing function is not exhibited before movement of the engaging section past the elastic deformable section.

This ensures that when the protector in the first position is about to be moved again to the second position, the engagement preventing function of the engagement preventing member is not exhibited and the engaging section comes into engagement with the elastic deformable section, whereby movement of the protector toward the side of the second position can be prevented more reliably.

In addition, in the puncture needle assembly according to the present invention, preferably, when the protector moves from the second position to the first position, the engagement preventing member remains on a base end side relative to the elastic deformable section, whereby the engagement preventing function is not exhibited.

This ensures that when the protector in the first position is about to be moved again to the second position, the engagement preventing function of the engagement preventing member is not exhibited and the engaging section comes into engagement with the elastic deformable section, whereby the protector can be inhibited more securely from moving toward the side of the second position.

Further, in the puncture needle assembly according to the present invention, preferably, when the protector moves from the second position to the first position, the engaging section is capable of pressing the elastic deformable section outwardly to thereby elastically deform the elastic deformable section.

This ensures that when the protector moves from the second position to the first position, the elastic deformable section undergoes elastic deformation, and the engaging section of the protector can move past (beyond) the elastic deformable section.

In addition, in the puncture needle assembly according to the present invention, preferably, the elastic deformable section is composed of small pieces, each of which is formed to project toward the distal end side (in the distal direction) and is inclined relative to the axis of the needle tube.

This ensures that when distal portions of the small pieces are pressed from the inside toward the outside, the small pieces are deformed (elastically deformed) so as to turn with the base end portion thereof acting as a fulcrum. Then, when the pressing force is released, each of the small pieces is restored into its original shape (state) under its own elasticity (self-restoring force).

Further, in the puncture needle assembly according to the present invention, preferably, the plural small pieces are arranged intermittently around the axis of the needle tube.

This ensures that the area of engagement (area of contact) between the small pieces and the engaging section can be made comparatively large, and therefore, engagement between the engaging section and the small pieces occurs more securely.

In addition, in the puncture needle assembly according to the present invention, preferably, when the protector is in the first position, the elastic deformable section is in a natural state with no external forces exerted thereon.

This ensures that, even when the puncture needle assembly is stored for a long period of time, each of the small pieces is prevented reliably from acquiring an unintentional semi-permanent deformation (semi-permanent bend) therein. Therefore, the shapes of the small pieces are maintained, and the small pieces can be deformed elastically in a preferable manner.

Further, in the puncture needle assembly according to the present invention, preferably, the elastic deformable section is disposed at a distal portion of the body, and the engaging section is disposed at a base end portion of the protector.

This enables the protector to move from the first position to the second position.

In addition, in the puncture needle assembly according to the present invention, preferably, the biasing means is composed of a coil spring, which makes contact with a side of the protector on the distal end side thereof, and further makes contact with a side of the body on a base end side thereof.

This ensures that the protector can reliably be biased toward the distal end side (i.e., in the distal direction).

Further, in the puncture needle assembly according to the present invention, preferably, the protector has a contact section that comes into contact with a part on the distal end side relative to the elastic deformable section of the body when the protector is in the first position, wherein contact of the contact section with the body inhibits the protector in the first position from becoming released from the body.

This prevents the protector from being moved further toward the distal end side (i.e., further from the first position). Therefore, the protector is prevented (inhibited) from slipping off (becoming released) from the body.

In addition, in the puncture needle assembly according to the present invention, preferably, whether the puncture needle assembly is unused or used can be distinguished.

This makes it possible to securely distinguish between unused and used conditions of the puncture needle assembly.

Further, in order to achieve the aforementioned object, the present invention also provides a medicinal liquid injector including:

the puncture needle assembly according to the present invention; and a container having a mounting section on which the hub of the puncture needle assembly is mounted, and which is preliminarily filled with a medicinal liquid.

This ensures that the needle point of the needle tube can be securely prevented from becoming unintentionally exposed from the protector.

BRIEF DESCRIPTION OF THE DRAWINGS

FIG. 5 is a longitudinal sectional view sequentially illustrating states during use of the medicinal liquid injector shown in FIG. 1;

FIG. 7 is a longitudinal sectional view illustrating a condition in which use of the medicinal liquid injector shown in FIG. 1 is stopped halfway;

BEST MODE FOR CARRYING OUT THE INVENTION

A puncture needle assembly and a medicinal liquid injector according to the present invention will be described in detail below, based on preferred embodiments of the present invention, as shown in the accompanying drawings.

First Embodiment

Figure 1:
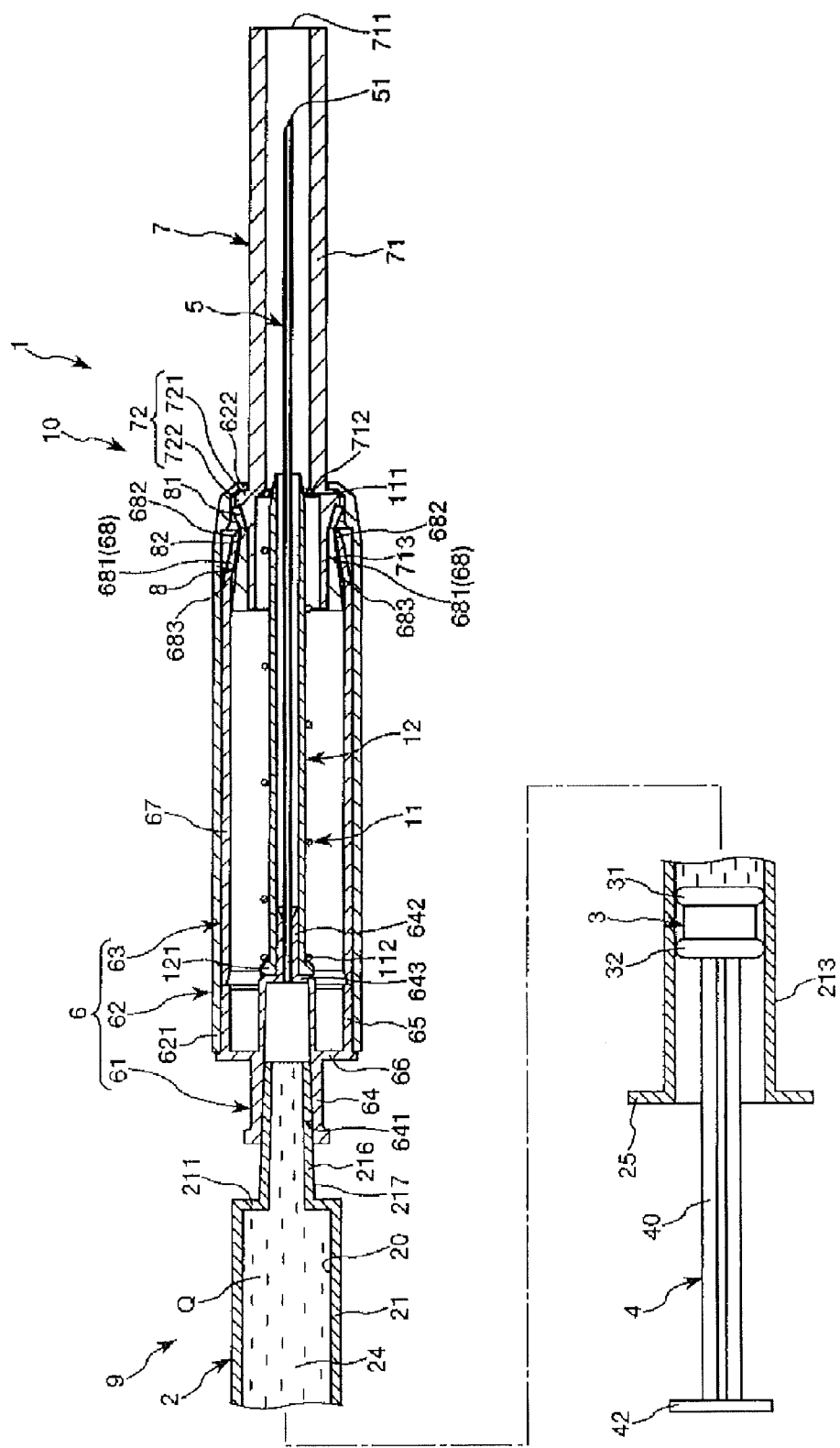
FIG. 1 is a longitudinal sectional view sequentially illustrating states during use of a first embodiment of a medicinal liquid injector (puncture needle assembly) according to the present invention.
Figure 2:
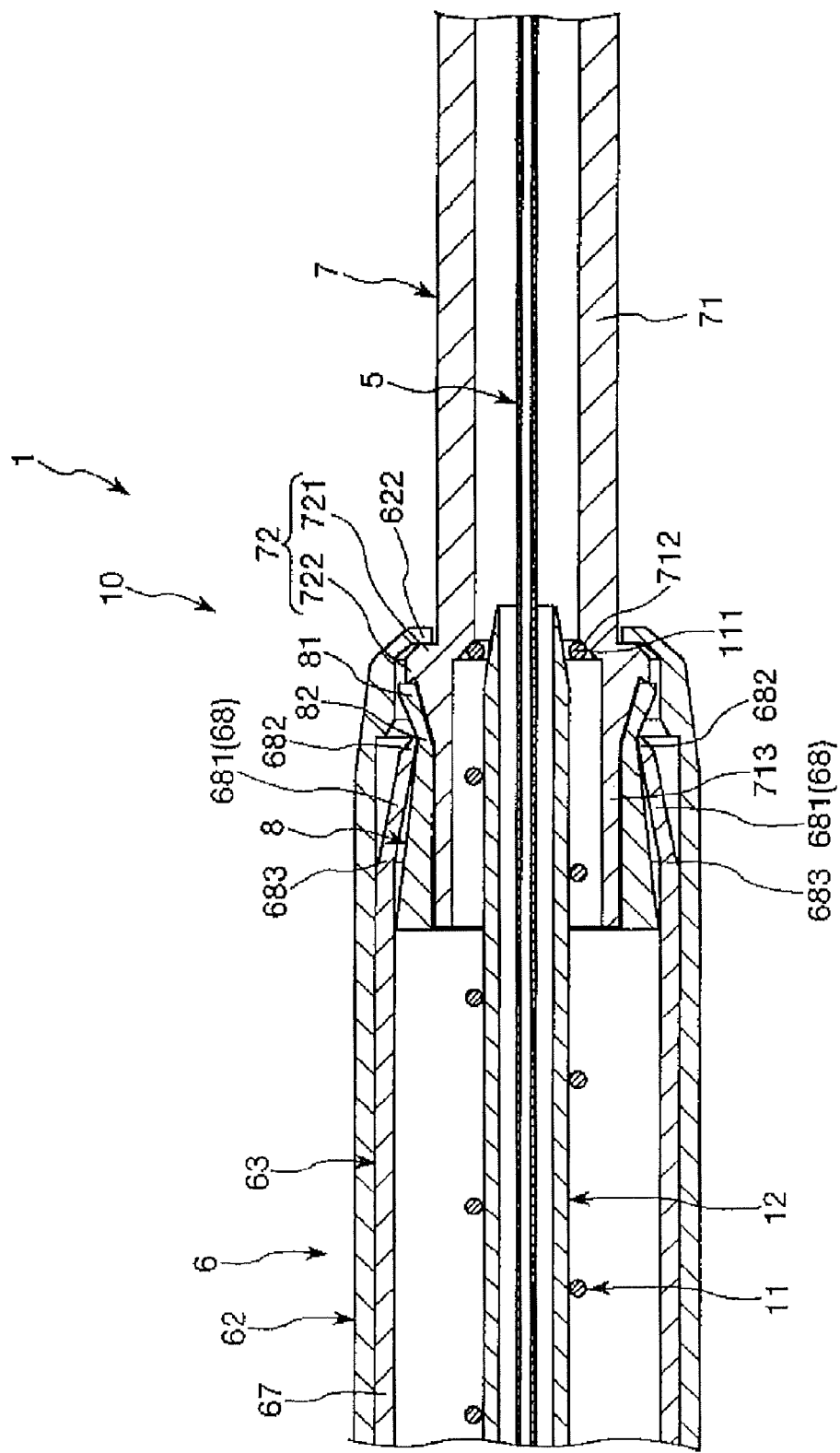
FIG. 2 is a longitudinal sectional view showing, in an enlarged form, a major part of the medicinal liquid injector shown in FIG. 1.

FIG. 1 is a longitudinal sectional view sequentially illustrating states during use of a first embodiment of the medicinal liquid injector (puncture needle assembly) according to the present invention. FIG. 2 is a longitudinal sectional view showing, in an enlarged form, a major part of the medicinal liquid injector shown in FIG. 1. FIGS. 3 to 6 are longitudinal sectional views sequentially illustrating states during use of the medicinal liquid injector shown in FIG. 1. FIG. 7 is a longitudinal sectional view illustrating a condition in which use of the medicinal liquid injector shown in FIG. 1 is stopped halfway. Incidentally, in the following explanations, to facilitate descriptions thereof, the left side in FIGS. 1 to 7 will be referred to as a "base end (proximal end)", while the right side will be referred to as a "distal end."

The medicinal liquid injector 1 shown in each of the drawings is composed of a syringe (container) 9 prefilled with a medicinal liquid Q, and a puncture needle assembly 10 mounted on the syringe 9. The medicinal liquid injector 1 is used for injecting (administering) the medicinal liquid Q into a living body. Incidentally, the medicinal liquid Q filled in the medicinal liquid injector 1 (syringe 9) is appropriately selected according to the intended use thereof. Examples of such medicinal liquids Q include medicines used mainly for hypodermic injection and intramuscular injection, such as hematinics, vaccines, hormone products, antirheumatics, carcinostatics, anesthetics, anticoagulants, etc.

Next, configurations of components will be described below.

The syringe 9 has an outer tube (syringe outer tube) 2 having a bottomed tubular shape, a gasket 3 that is slidable in the outer tube 2, and a plunger 4, which is connected to a base end portion of the gasket 3.

The outer tube 2 is composed of a bottomed tubular member having a bottom section 211, and the outer tube 2 is formed with a mouth section (mounting section) 216 projecting toward the distal end side (in the distal direction) from the bottom section 211. A body 6 of the puncture needle assembly 10 is mounted onto the mouth section 216. By operating the plunger 4 so as to move in a condition where the puncture needle assembly 10 is mounted onto the mouth section 216, the medicinal liquid Q is caused to flow through the mouth section 216 and into the puncture needle assembly 10 (see FIG. 3). In addition, the mouth section 216 has an outside diameter that decreases gradually toward the distal end side (in the distal direction), and the outer peripheral portion 217 thereof is tapered. More specifically, the outer peripheral portion 217 of the mouth section 216 forms a Luer taper.

The outer tube 2 (outer tube body 21) includes a plate-shaped flange 25, which is formed integrally on the outer periphery of the base end thereof. For example, when operating the plunger 4 so as to move relative to the outer tube 2, such an operation can be carried out by placement of a finger or fingers on the flange 25.

Examples of materials constituting the outer tube 2 and the plunger 4 (described later) may include various resins such as cyclic polyolefins, polyvinyl chloride, polyethylene, polypropylene, polystyrene, poly(4-methylpentene-1), polycarbonate, acrylic resin, acrylonitrile-butadiene-styrene copolymer, and polyesters such as polyethylene terephthalate, etc., butadiene-styrene copolymer, polyamides, polyether-sulfones, polysulfones, etc. Among these materials, resins such as cyclic polyolefins, polypropylene, polyesters, poly(4-methylpentene-1), polyether-sulfones, polysulfones, etc., are preferred due to their easy moldability. Incidentally, the material constituting the outer tube 2 preferably is substantially transparent, for enabling visibility of the inside of the outer tube 2.

Additionally, the outer tube 2 preferably is provided with graduations (not shown) on an outer peripheral portion 213 (outer peripheral surface) thereof. This makes it possible to grasp the amount of the medicinal liquid Q contained in the medicinal liquid injector 1.

As described above, the gasket 3, which is formed of an elastic material, is contained in the outer tube 2. The gasket 3 is provided at an outer peripheral portion thereof with two ring-shaped projections 31 and 32, which are separated by a predetermined interval in the axial direction. The projections 31, 32 are slid while being kept in secure contact with an inner peripheral surface 20 of the outer tube 2, such that air-tightness (liquid-tightness) can be securely maintained and slidability is enhanced. In addition, a space 24 surrounded by the gasket 3 and the outer tube 2 can be filled with the medicinal liquid Q.

Examples of materials constituting the gasket 3 include various rubber materials (especially vulcanized rubbers) such as natural rubber, isoprene rubber, butadiene rubber, styrene-butadiene rubber, nitrile rubber, chloroprene rubber, butyl rubber, acrylic rubber, ethylene-propylene rubber, hydrin rubber, urethane rubber, silicone rubber, fluoro-rubber, etc., various thermoplastic elastomers based on styrene, polyolefin, polyvinyl chloride, polyurethane, polyester, polyamide, polybutadiene, transpolyisoprene, fluoro-rubber, chlorinated polyethylene or the like, and comparatively flexible resin materials such as polyethylene, polyvinyl chloride resin, etc. Such materials can be used either singly or in a combination of two or more thereof.

The plunger 4 is connected to a base end portion of the gasket 3. The plunger 4 performs an operation of moving the gasket 3 in the outer tube 2 along the axial direction thereof. Incidentally, the method for connecting the plunger 4 to the gasket 3 is not particularly limited. Examples of applicable methods include screwing and fitting.

The plunger 4 principally comprises a body 40 composed of a plate piece formed in the shape of a cross when viewed in cross-section. At the base end of the plunger 4, a flange-like (plate-like) finger holder section 42 is formed integrally with the body 40. By pushing the finger holder section 42 with a finger or the like, the plunger 4 is operated to move toward the distal end side (in the distal direction).

As shown in each of the drawings, the puncture needle assembly 10, which is mounted onto the mouth section 216 of the syringe 9, includes a needle tube (hollow needle) 5, a body 6 having a hub (needle hub) 61 for supporting the needle tube 5, a protector 7 capable of covering the needle tube 5 (needle point 51), a coil spring (biasing member) 11 serving as a biasing means for biasing the protector 7, and an engagement preventing member 8 contained in the body 6.

The needle tube 5 has a sharp needle point 51 formed at the distal end thereof. The shape of the needle point 51 is not particularly limited. In the present embodiment, the needle point 51 is formed with a cutting edge surface (bevel) thereof inclined at a predetermined angle relative to the axis of the needle tube 5.

The needle tube 5 is formed from a metallic material such as, for example, stainless steel, aluminum or aluminum alloy, or titanium or titanium alloy.

The body 6 includes the hub 61, a tubular outside member (connecting member) 62 connecting the hub 61 and the protector 7 to each other, and an inside member 63 disposed (contained) inside the outside member 62.

The hub 61 is composed of a tubular inner tube section 64, a tubular outer tube section 65 provided on an outer peripheral side of the inner tube section 64, and a connecting section 66, which interconnects the inner tube section 64 and the outer tube section 65.

Concerning the inner tube section 64, a base end portion thereof forms a part into which the mouth section 216 of the syringe 9 is inserted. An inner peripheral portion 641 of the inner tube section 64 is tapered similarly to the outer peripheral portion 217 of the mouth section 216. This ensures that when the mouth section 216 of the syringe 9 is inserted into the inner tube section 64, the outer peripheral portion 217 of the mouth section 216 and the inner peripheral portion 641 of the inner tube section 64 make secure contact with each other. Accordingly, the puncture needle assembly 10 can be mounted (connected) to the syringe 9 in a liquid-tight manner.

A distal portion 642 of the inner tube section 64 is reduced in outside diameter and inside diameter. The inside diameter of the distal portion 642 is set to be comparable to or slightly smaller than the outside diameter of the needle tube 5. This ensures that a base end portion of the needle tube 5 fits securely in the distal portion 642, whereby the needle tube 5 can be fixed in place.

The connecting section 66 is formed to project from an intermediate part of the outer peripheral portion of the inner tube section 64, and is flange-like in shape. The inner tube section 64 and the outer tube section 65 are interconnected through the connecting section 66.

Incidentally, in the hub 61, the inner tube section 64, the outer tube section 65 and the connecting section 66 may be formed integrally with one another. Alternatively, a configuration may be adopted in which such sections are formed as separate bodies, which are connected and fixed to one another.

The outside member 62 is tubular in shape. The outside member 62 has a base end portion 621 thereof fitted onto the outer tube section 65 of the hub 61 from the outer peripheral side, whereby the outside member 62 is fixed to the hub 61. Incidentally, the outside member 62 and the hub 61 may be secured (fixed) to each other, for example, by fusing, by adhesion with an adhesive, etc., or the outside member 62 and the hub 61 may be fixed to each other using a combination of these methods.

At an inner peripheral portion of the distal end of the outside member 62, a rib (projecting section) 622 is formed to project toward the side of the needle tube 5 (inside) along the circumferential direction and over one circumference. In other words, the rib 622 has a ring-like shape, with the center axis (axis) of the needle tube 5 serving as the center of the ring. The inside diameter of the rib 622 is set to be slightly larger than the outside diameter of a protector body 71 of the protector 7, which will be described later.

The inside member 63 includes a tubular section 67, which is tubular in the same manner as the outer tube section 65 of the hub 61, and an elastic deformable section 68, which is provided at a distal portion of the tubular section 67 and which is elastically deformable.

The tubular section 67 makes up a part for fixing the inside member 63 relative to the hub 61 and the outside member 62. Examples of securing (fixing) methods include such methods as fitting, fusing, adhesion with an adhesive, etc., and combinations of such methods.

The tubular section 67 and the outside member 62 constitute a tubular body section of the body 6. The hub 61 is fixed to a base end portion of the tubular body section, and a portion (a part of the needle tube 5), which ranges from an intermediate portion to the base end portion of the needle tube 5, is inserted into the tubular body section.

The elastic deformable section 68 is provided on the distal end side relative to the base end portion of the tubular body section. More specifically, the elastic deformable section 68 is composed of a plurality of (in this embodiment, two) small pieces 681, which are formed to project in plate-like shapes along the distal direction from the distal end of the tubular section 67. These small pieces 681 are located at a distal portion of the outside member 62 (body 6), and are arranged intermittently around the axis of the needle tube 5. In the present embodiment, the small pieces 681 are disposed to face each other with the needle tube 5 disposed therebetween, that is, the small pieces 681 are disposed at an interval (angular interval) of 180°. Incidentally, distal portions 682 of the small pieces 681 are located on the base end side relative to the ribs 622 of the outside member 62.

In addition, as shown in FIGS. 1 and 2, each of the small pieces 681 is disposed so that one surface thereof is oriented toward the inside (toward the side of the needle tube 5), whereas the other surface thereof is oriented toward the outside (the side opposite to the needle tube 5). Further, each of the small pieces 681 is inclined relative to the axis of the needle tube 5, so that the distal portion 682 thereof is closer to the needle tube 5 than the base portion (base end portion) 683.

When each of the small pieces 681 are placed in such a posture, it is ensured that when the distal portion 682 of each small piece 681 is pressed from the inside toward the outside (i.e., in the vertical direction in FIGS. 1 and 2), each of the small pieces 681 becomes deformed (elastically deformed) so as to turn with the base portion 683 thereof acting as a fulcrum. Then, when the pressing force is released, under its own elasticity (self-restoring force), each of the small pieces 681 is restored into its original shape (state).

When the protector 7 (described later) is in a first position (described later), and in particular, when the puncture needle assembly 10 (medicinal liquid injector 1) is in an unused state (the state shown in FIGS. 1 and 2), the elastic deformable section 68, which is composed of the small pieces 681 as mentioned above, is in a natural state with no external forces being exerted thereon. This ensures that, even when the puncture needle assembly 10 is stored for a long period of time, the elastic deformable section 68 (small pieces 681) is securely prevented from unintentionally acquiring a semi-permanent deformation (semi-permanent bend) therein. Accordingly, the shape of the elastic deformable section 68 is maintained, whereby the elastic deformable section 68 can be elastically deformed in a preferred manner.

As mentioned above, the hub 61, the outside member 62 and the inside member 63 (elastic deformable section 68) constituting the body 6 are formed as separate members (separate bodies). Although in the present embodiment, such members are connected and fixed to one another, the body 6 may be composed of a single member.

Incidentally, the materials constituting the body 6, the protector 7 and the engagement preventing member 8 are not particularly limited. For example, materials similar to those described above as materials for the outer tube 2 can be used.

Figure 4:
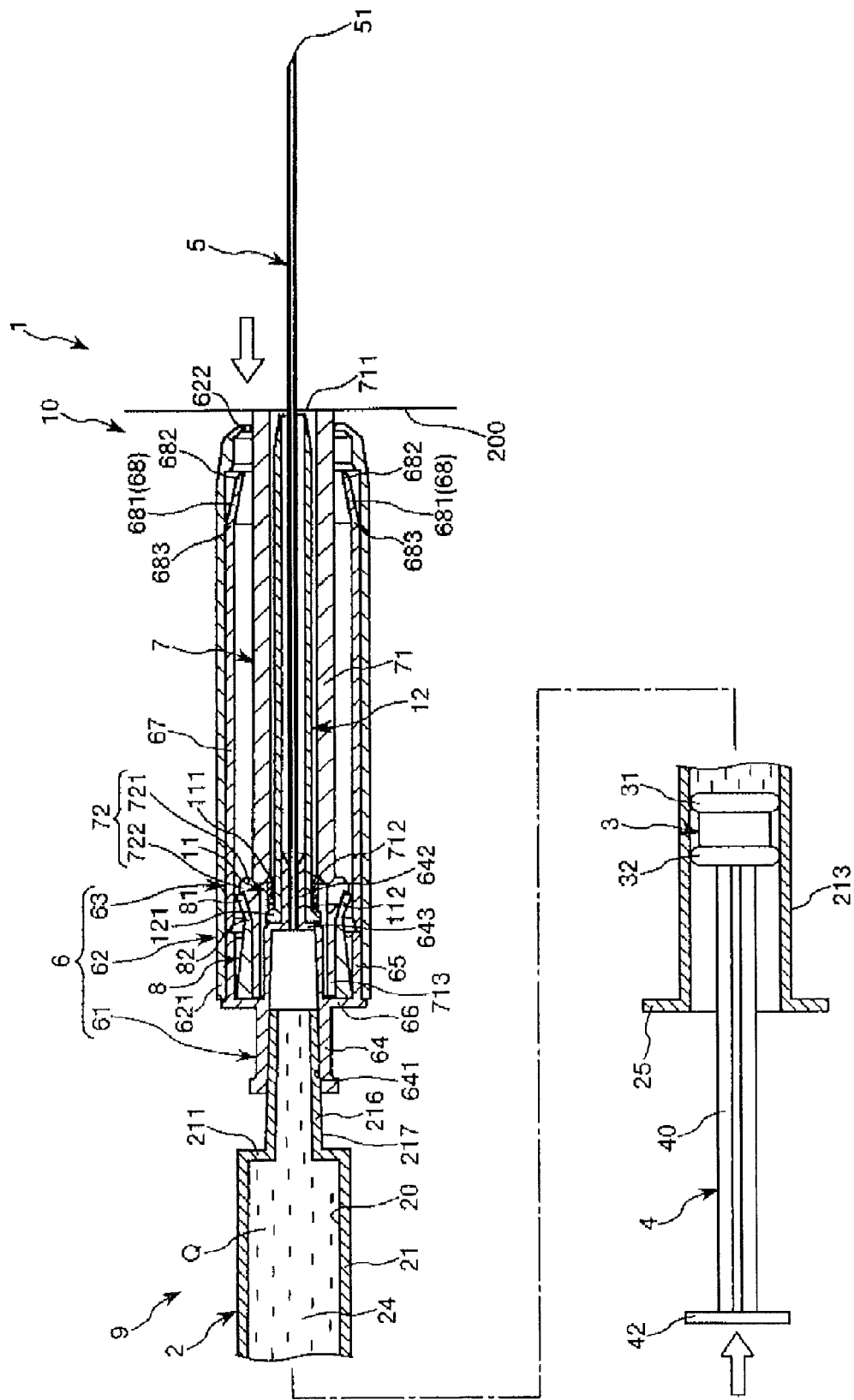
FIG. 4 is a longitudinal sectional view sequentially illustrating states during use of the medicinal liquid injector shown in FIG. 1.
Figure 6:
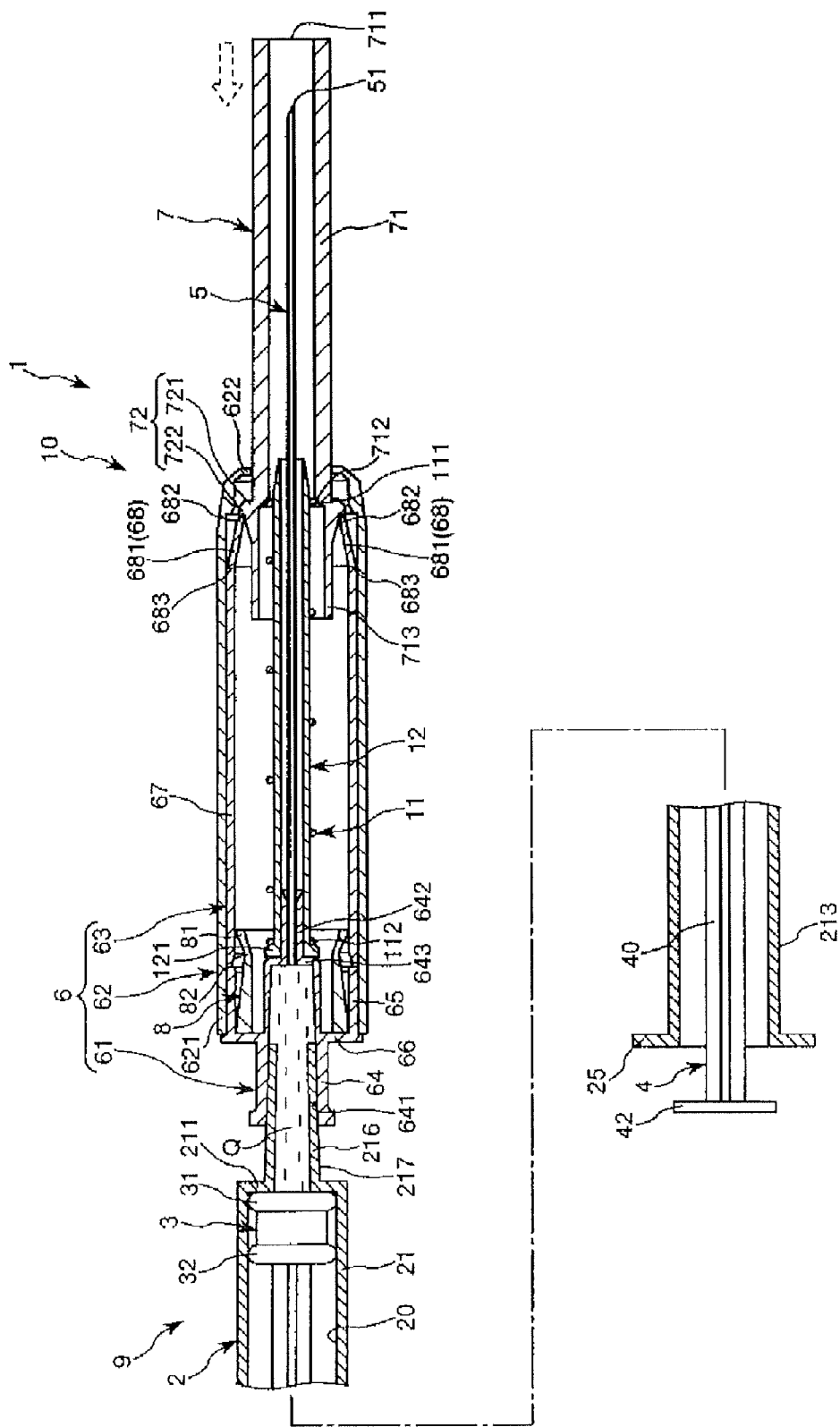
FIG. 6 is a longitudinal sectional view sequentially illustrating states during use of the medicinal liquid injector shown in FIG. 1.

The protector 7 is supported on the body 6 so as to be movable along the axial direction of the needle tube 5. More specifically, the protector 7 is supported so as to be movable along the axial direction of the needle tube 5 between a first position, as shown in FIGS. 1, 2 and 5 to 7, at which the protector 7 covers the needle point 51 of the needle tube 5, and a second position, as shown in FIG. 4, at which the protector 7 is retracted from the first position and the needle point 51 is exposed. Incidentally, the second position is on the base end side (proximal side) relative to the first position.

The protector 7 has a tubular protector body 71, and a rib (projecting section) 72 provided at a base end portion 713 of the protector body 71.

The protector body 71 has a tubular shape, which is open at both distal and base ends thereof. When the protector 7 is in the second position, as shown in FIG. 4, the needle point 51 protrudes from a distal opening 711 of the protector body 71. This ensures that a living body surface (target part) 200 can be punctured with the needle point 51. Further, in this condition (puncturing condition), when an operation is performed to push the plunger 4, a medicinal liquid Q can be administered (injected) into the living body.

The rib 72 is formed on an outer peripheral part of the base end portion 713 of the protector body 71 so as to project toward a side (outside) opposite to the needle tube 5, along the circumferential direction of the protector body 71 and over one circumference thereof. In other words, the rib 72 is ring-like in shape, with a center axis (axis) of the needle tube 5 located at the center of the ring. The rib 72 is contained within the body 6, such that when the protector 7 is in the first position, the rib 72 is located between the rib 622 of the outside member 62 and the small pieces 681 (elastic deformable section 68). A portion on the distal end side (distal side) of the rib 72 forms a contact section 721, which makes contact with the rib 622 of the outside member 62. A portion on the base end side of the rib 72 forms an engaging section 722 that engages with the small pieces 681 (elastic deformable section 68).

The outside diameter of the contact section 721 is set to be greater than the inside diameter of the rib 622 of the outside member 62. This permits the contact section 721 to make contact with the rib 622 of the outside member 62. More specifically, when the protector 7 is in the first position, the contact section 721 comes into contact with the rib 622 of the outside member 62 (see FIGS. 1, 2 and 5). This ensures that the protector 7 is prevented from moving further in the distal direction (away from the first position), so that the protector 7 can be prevented (inhibited) from slipping off (becoming released) from the body 6.

On the other hand, the engaging section 722 projects not only toward the outside, but also further toward the base end side. More specifically, as viewed in longitudinal cross-section, a base end portion of the engaging section 722 has an angular part (in the configuration shown in the drawings, an acute angular part), which is oriented toward the base end side. In addition, in a natural state of the elastic deformable section 68, the outside diameter of the engaging section 722 is set to be larger than the interval between the distal portions 682 of the two small pieces 681. This permits the engaging section 722 to engage with the small pieces 681 (elastic deformable section 68). More specifically, when the protector 7 has moved from the first position to the second position and then returns again to the first position (i.e., when the protector 7 is in the first position), the engaging section 722 engages with the small pieces 681 (see FIG. 6). This prevents (inhibits) the protector 7 from moving toward the side of the second position, whereby the protector 7 can reliably be prevented from moving again toward the second position. Accordingly, once having been used, the needle point 51 of the needle tube 5 can reliably be prevented from becoming unintentionally exposed from the protector 7.

In addition, as mentioned above, the small pieces 681 are arranged intermittently around the axis of the needle tube 5. Therefore, the area of engagement (area of contact) of the small pieces 681 with the engaging section 722 can be made comparatively large, and accordingly, the engaging section 722 and the elastic deformable section 68 are kept in engagement more securely.

Further, the engaging section 722 (rib 72) has a function of pressing the elastic deformable section 68 outwardly, so that the elastic deformable section 68 becomes deformed when the protector 7 moves from the second position to the first position. This ensures that when the protector 7 moves from the second position to the first position, the elastic deformable section 68 is elastically deformed, and the rib 72 (more specifically the engaging section 722) of the protector 7 can move past (beyond) the small pieces 681 (elastic deformable section 68).

Incidentally, the rib 72 need not necessarily be formed over one circumference, insofar as the rib 72 is formed at positions corresponding to the small pieces 681 of the protector body 71, i.e., at positions where the rib 72 can engage with the small pieces 681 (elastic deformable section 68). For example, the rib 72 may be formed in a shape obtained by partially cutting out a portion having a ring-like shape (ring-like portion), e.g., a C-shape or the like, or a plurality of ribs may be arranged intermittently.

In the interior of the inside member 63 (elastic deformable section 68) of the body 6, the engagement preventing member 8, which is in a state of being mounted to the protector 7, is movable along the axial direction of the needle tube 5. When the protector 7 moves from the first position toward the second position (i.e., when the protector 7 moves from the first position to the second position), the engagement preventing member 8 moves together with the protector 7 and comes into contact with the engaging section 722 (covers the engaging section 722) while exhibiting an engagement preventing function, thereby permitting the engaging section 722 to move past (beyond) the elastic deformable section 68 without coming into engagement with the elastic deformable section 68. In other words, the engagement preventing member 8 moves together with the protector 7 when the protector moves from the first position to the second position, thereby inhibiting engagement of the engaging section 722 with the elastic deformable section 68 and causing elastic deformation of the elastic deformable section 68. This ensures that when the protector 7 moves from the first position to the second position, the rib 72 (specifically the engaging section 722 thereof) of the protector 7 does not come into engagement with the distal portions 682 of the small pieces 681, and thus the protector 7 can move past the distal portions 682.

The engagement preventing member 8 is tubular in shape, and is removably mounted on the base end portion 713 of the protector body 71, i.e., an outer peripheral portion on the base end side of the engaging section 722 of the protector body 71. (Stated otherwise, the base end portion 713 of the protector body 71 is inserted into the engagement preventing member 8).

In a condition (hereinafter referred to simply as a "mounted condition") in which the engagement preventing member 8 is mounted on the protector 7 (the base end portion 713 of the protector body 71), the distal end (distal portion 81) of the engagement preventing member 8 and the engaging section 722 of the protector 7 are in contact, or are capable of coming into contact, with each other. This ensures that when the protector 7 is moved from the first position to the second position, the engagement preventing member 8 can move reliably together with the protector and can exhibit the engagement preventing function (the protector 7 can move together with the engagement preventing member 8).

In addition, in the mounted condition when the protector 7 is in the first position, the elastic deformable section 68 is located on the outer peripheral side of the engagement preventing member 8, and distal portions 682 of the small pieces 681 (elastic deformable section 68) are located at an intermediate portion of the engagement preventing member 8, and more specifically, at a minimum outside diameter portion 82 (described later) of the engagement preventing member 8.

A distal portion 81 of the engagement preventing member 8 forms a part which, when the engagement preventing member 8 moves from the first position to the second position together with the protector, comes into contact with the engaging section 722, thus inhibiting the engaging section 722 from coming into engagement with the elastic deformable section 68, and pressing the elastic deformable section 68 outwardly, thereby elastically deforming the elastic deformable section 68.

The outside diameter of the distal end of the engagement preventing member 8 is set so as not to be less than the outside diameter of the engaging section 722 (i.e., the outside diameter at the engaging section 722 of the protector 7). This ensures that when the protector 7 moves from the first position to the second position, the engaging section 722 can be inhibited reliably from coming into engagement with the elastic deformable section 68, and the elastic deformable section 68 can become elastically deformed and made capable of moving past the engaging section 722 (rib 72).

In addition, the outside diameter of the distal portion 81 of the engagement preventing member 8 gradually increases from the base end side toward the distal end side thereof, and conversely, the outside diameter of a portion on the base end side relative to the distal portion 81 of the engagement preventing member 8 gradually increases from the distal end side toward the base end side thereof. Incidentally, at a portion (boundary part) where the variation (increase or decrease) in the outside diameter of the engagement preventing member 8 is reversed, a minimum outside diameter portion 82 is formed where the outside diameter of the engagement preventing member 8 is minimized. Since the outside diameter of the distal portion 81 of the engagement preventing member 8 gradually increases from the base end side toward the distal end side, the elastic deformable section 68 can be elastically deformed in a smooth manner when the protector 7 moves from the first position to the second position.

In addition, the engagement preventing member 8 is configured such that, when the protector 7 moves or returns again toward the first position after the engagement preventing member 8 has moved together with the protector 7 from the first position to the second position, the engagement preventing member 8 is released from the protector 7 (the base end portion 713 of the protector body 71), so that only the protector 7 returns again to the first position. This ensures that when the protector 7 has returned again to the first position, as mentioned above, the engaging section 722 engages with the small pieces 681 (elastic deformable section 68), whereby the protector 7 can reliably be prevented from moving again toward the second position.

Further, in the mounted condition, a minute gap is formed between an inner peripheral surface of the engagement preventing member 8 and an outer peripheral surface of the base end portion 713 of the protector body 71. This ensures that when the engagement preventing member 8 is released from the protector 7, i.e., when the protector 7 moves from the second position to the first position, the engagement preventing member 8 can be released smoothly and assuredly.

In addition, the outside diameters of the distal end and the base end of the engagement preventing member 8 both are set to be slightly smaller than the inside diameter of the tubular section 67 of the inside member 63. Thus, the protector 7 is movably supported in the tubular section 67 (inside member 63) through the engagement preventing member 8. On the other hand, as mentioned above, the inside diameter of the rib 622 of the outside member 62 is set to be slightly greater than the outside diameter of the protector body 71, whereby the protector 7 is movably supported by the rib 622 (outside member 62). Therefore, the tubular section 67 of the inside member 63 and the rib 622 of the outside member 62 function as guide sections for guiding the movable protector 7 when the protector 7 moves from the first position to the second position (i.e., when the protector 7 moves between the first position and the second position). This enables the protector 7 to move in a stable manner.

Incidentally, in the configuration shown in the drawings, the position of the base end of the engagement preventing member 8 and the position of the base end of the protector 7 coincide with each other in the axial direction of the needle tube 5. However, the invention is not limited to this configuration. One of the base end of the engagement preventing member 8 and the base end of the protector 7 may be located more toward the base end side relative to the other member.

A coil spring 11 is disposed between the body 6 and the protector 7. Concerning the coil spring 11, the distal end 111 thereof is in contact with a stepped part 712 (protector 7 side) where the inside diameter of the protector body 71 (protector 7) changes abruptly. In addition, the base end 112 of the coil spring 11 is in contact with a flange 121 (body 6 side) formed on an outer periphery of the base end of a buckling preventive member 12, which will be described later. Incidentally, the flange 121 is in contact with a stepped part 643, which is formed at a distal portion of the inner tube section 64.

With the coil spring 11 disposed in this manner, the protector 7 can be securely biased by the coil spring 11 in the distal direction, or in other words, from the second position toward the first position.

Incidentally, the material constituting the coil spring 11 is not particularly limited. Metallic materials such as stainless steel can be used.

In addition, the body 6 is provided therein with a buckling preventive member 12, which is inserted into the coil spring 11. The buckling preventive member 12 is tubular in shape, and a base end portion thereof is fitted to a distal portion 642 of the inner tube section 64 of the hub 61. When the coil spring 11 is compressed under pressure from the protector 7, which is displaced to the second position (see FIG. 4), the buckling preventive member 12 supports the coil spring 11 from the inside thereof, thereby preventing the coil spring 11 from buckling.

Next, states during use (operations) of the medicinal liquid injector 1 will be described below.

[1] First, the medicinal liquid injector 1, which is preliminarily filled with a medicinal liquid Q in an amount sufficient for administration into a living body, is prepared (see FIG. 1). At this time, the medicinal liquid injector 1 is in an unused state, in which the protector 7, which is fitted with the engagement preventing member 8 at the base end portion 713, is in the first position. This ensures that the needle tube 5 remains covered at a portion ranging to the needle point 51, so that mistaken punctures with the needle point 51 are prevented from occurring.

Figure 3:
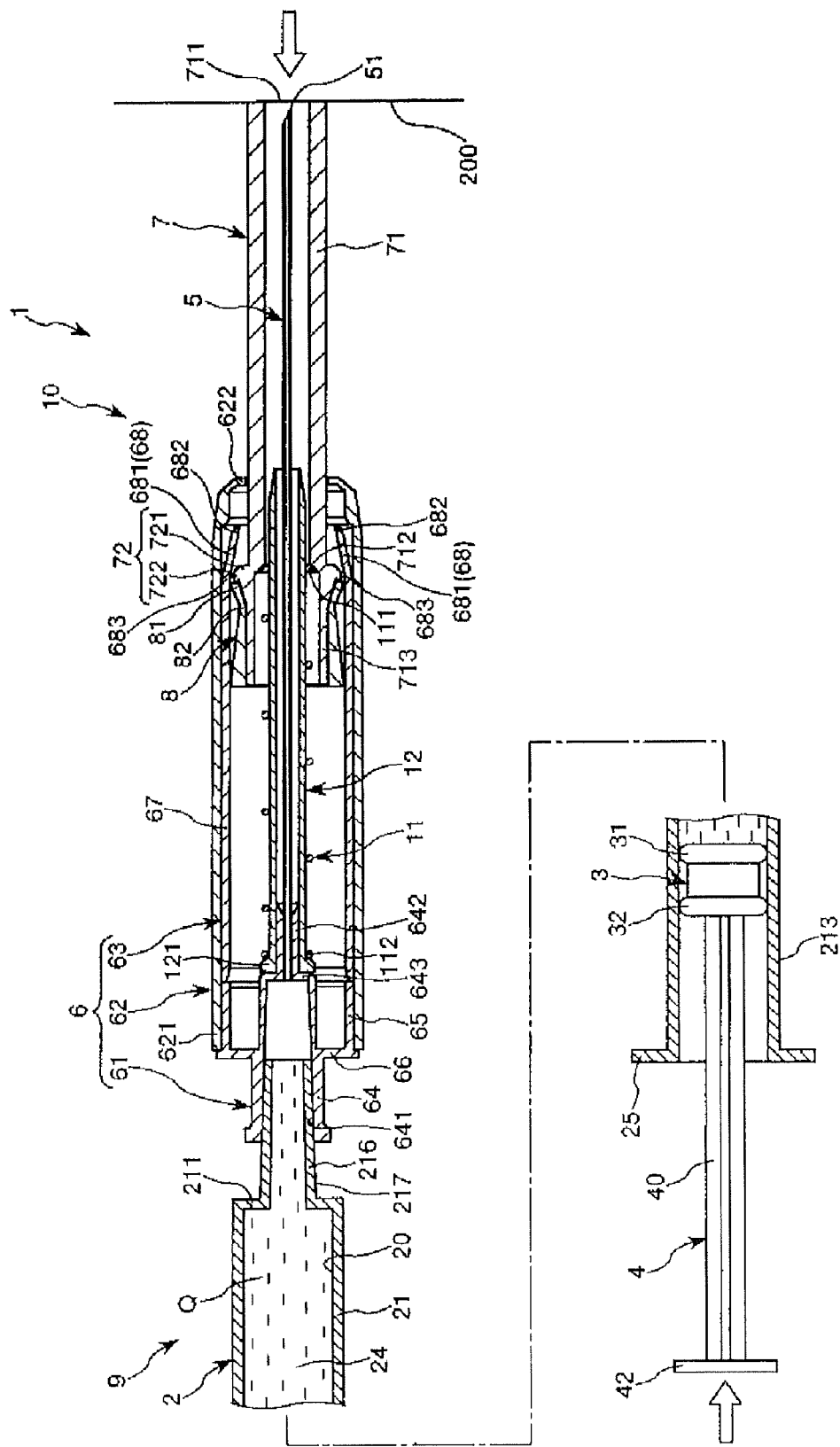
FIG. 3 is a longitudinal sectional view sequentially illustrating states during use of the medicinal liquid injector shown in FIG. 1.

[2] Next, while gripping the outer tube 2, the distal opening 711 of the protector 7, which is in the state shown in FIG. 1, is pressed against a puncture region (target site) of a living body surface 200 against the biasing force of the coil spring 11, whereupon the protector 7 is moved to the second position (see FIGS. 3 and 4). This causes the needle point 51 of the needle tube 5, having been covered with the protector 7, to protrude in the distal direction through the distal opening 711 of the protector 7 in order to puncture the living body surface 200 (see FIG. 4).

In addition, when the protector 7 and the engagement preventing member 8 are moved toward the second position, the distal portion 81 of the engagement preventing member 8, while making contact with the engaging section 722 (rib 72) of the protector 7, presses the distal portions 682 of the small pieces 681 of the inside member 63 toward the outer side. As a result of such pressing, as mentioned above, the small pieces 681 are elastically deformed, respectively (i.e., the elastic deformable section 68 is pressed open wider). As a result, the distal portion 81 of the engagement preventing member 8 moves past the distal portions 682 of the small pieces 681, and the engaging section 722 (rib 72) of the protector 7 moves past the distal portions 682 of the small pieces 681 without coming into engagement with the distal portions 682. Thus, with the rib 72 having moved past the small pieces 681, the pressing forces exerted on the small pieces 681 are released, so that each of the small pieces 681 is restored to its original shape (state) under its own elasticity. In this manner, the engagement preventing function of the engagement preventing member 8 is exhibited, and engagement of the engaging section 722 (rib 72) with the small pieces 681 (elastic deformable section 68) is prevented (i.e., the engagement function is disabled), so that the rib 72 and the engagement preventing member 8 move past the small pieces 681 (elastic deformable section 68).

Further, movement of the protector 7 toward the second position is conducted until the base end of the protector 7 and the base end of the engagement preventing member 8 come into contact with the connecting section 66 (limit of movement) (see FIG. 4). As a result, it can be confirmed that the protector 7 has been securely located in the second position, and hence, that the needle point 51 protrudes from the protector 7.

[3] Subsequently, while maintaining the condition in which the living body surface 200 is punctured by the needle point 51 of the needle tube 5, the index finger and the middle finger of the hand that grips the outer tube 2 are placed on an edge portion of the flange 25 of the outer tube 2, whereas the thumb is placed on the finger holder section 42 of the plunger 4. Then, using the thumb, the finger holder section 42 is pushed toward the distal end side (see FIG. 4). By this operation, the gasket 3 is moved in the distal direction, so that the medicinal liquid Q is securely administered (injected) from the space 24 in the outer tube 2 into the living body, via the mouth section 216 of the outer tube 2, the inner tube section 64 of the body 6, and the needle tube 5.

[4] After administration of the medicinal liquid Q, the medicinal liquid injector 1 (protector 7) is separated from the living body surface 200. At this time, the pressure exerted on the protector 7 from the living body surface 200 is released, and the protector 7 becomes pressed (biased) in the distal direction by the restoring force (biasing force) of the coil spring 11, whereby the protector 7 moves toward and is returned to the first position (see FIG. 5). As a result, the needle tube 5 is covered again at a portion ranging to the needle point 51 thereof. Therefore, scattering of blood that may adhere to the needle point 51, as well as mistaken puncturing with the blood covered needle point 51 are prevented from occurring, so that blood borne infections can be prevented.

In addition, when the protector 7 moves toward the first position (returns to the first position), the engagement preventing member 8 is released from the base end portion 713 of the protector body 71 due to the frictional force between the engagement preventing member 8 and the outer tube section 65 of the hub 61, and the engagement preventing member 8 is left (remains) at the base end portion of the body 6, so that only the protector 7 moves toward and returns to the first position. More specifically, when the protector 7 returns to the first position, contact between the engagement preventing member 8 and the engaging section 722 (rib 72) is released prior to movement of the engaging section 722 (rib 72) past the small pieces 681 (elastic deformable section 68). The engagement preventing member 8 thus remains on the base end side relative to the small pieces 681, so that the engagement preventing function of the engagement preventing member 8 is not exhibited. Consequently, the engagement preventing function of the engagement preventing member 8 is not exhibited again.

Further, when the protector 7 returns to the first position, the engaging section 722 (rib 72) of the protector 7 presses the small pieces 681 of the inside member 63 outwardly. Under such pressing, the small pieces 681 respectively become elastically deformed (the elastic deformable section 68 is pressed open wider), whereby the rib 72 of the protector 7 moves past the distal portions 682 of the small pieces 681. Thus, with the rib 72 having moved past the small pieces 681, the pressing forces exerted on the small pieces 681 are released, so that each of the small pieces 681 is restored to its original shape (state) under its own elasticity.

[5] In the case that a pressing force toward the base end side is exerted on the protector 7, starting from the condition shown in FIG. 5, the protector 7 tends to move toward the second position. However, the engaging section 722 of the protector 7 comes into engagement with the distal portions 682 of the small pieces 681, whereby the protector 7 is inhibited (prevented) from moving toward the side of the second position (see FIG. 6). As a result, erroneous use of a medicinal liquid injector 1 that has already been used is prevented. More specifically, causing the needle tube 5 to protrude, and administering a medicinal liquid Q into a living body through the needle tube 5 can securely be prevented from occurring.

[6] In addition, in the case that use of the medicinal liquid injector 1 is stopped halfway, for example, in the state shown in FIG. 3, when the medicinal liquid injector 1 (protector 7) is separated from the living body surface 200, the pressure exerted on the protector 7 from the living body surface 200 is released. As a result, in the same manner as mentioned previously, the engagement preventing member 8 is released from the base end portion 713 of the protector body 71, and only the protector 7 returns to the first position. Then, when a pressing force toward the base end side is exerted on the protector 7, starting from this condition, the engaging section 722 of the protector 7 comes into engagement with the distal portions 682 of the small pieces 681, whereby the protector 7 is inhibited (prevented) from moving toward the side of the second position (see FIG. 7). Consequently, erroneous use of a medicinal liquid injector 1 that has already been used is prevented. More specifically, causing the needle tube 5 to protrude, and administering a medicinal liquid Q into a living body through the needle tube 5 can securely be prevented from occurring.

Second Embodiment

Figure 8:
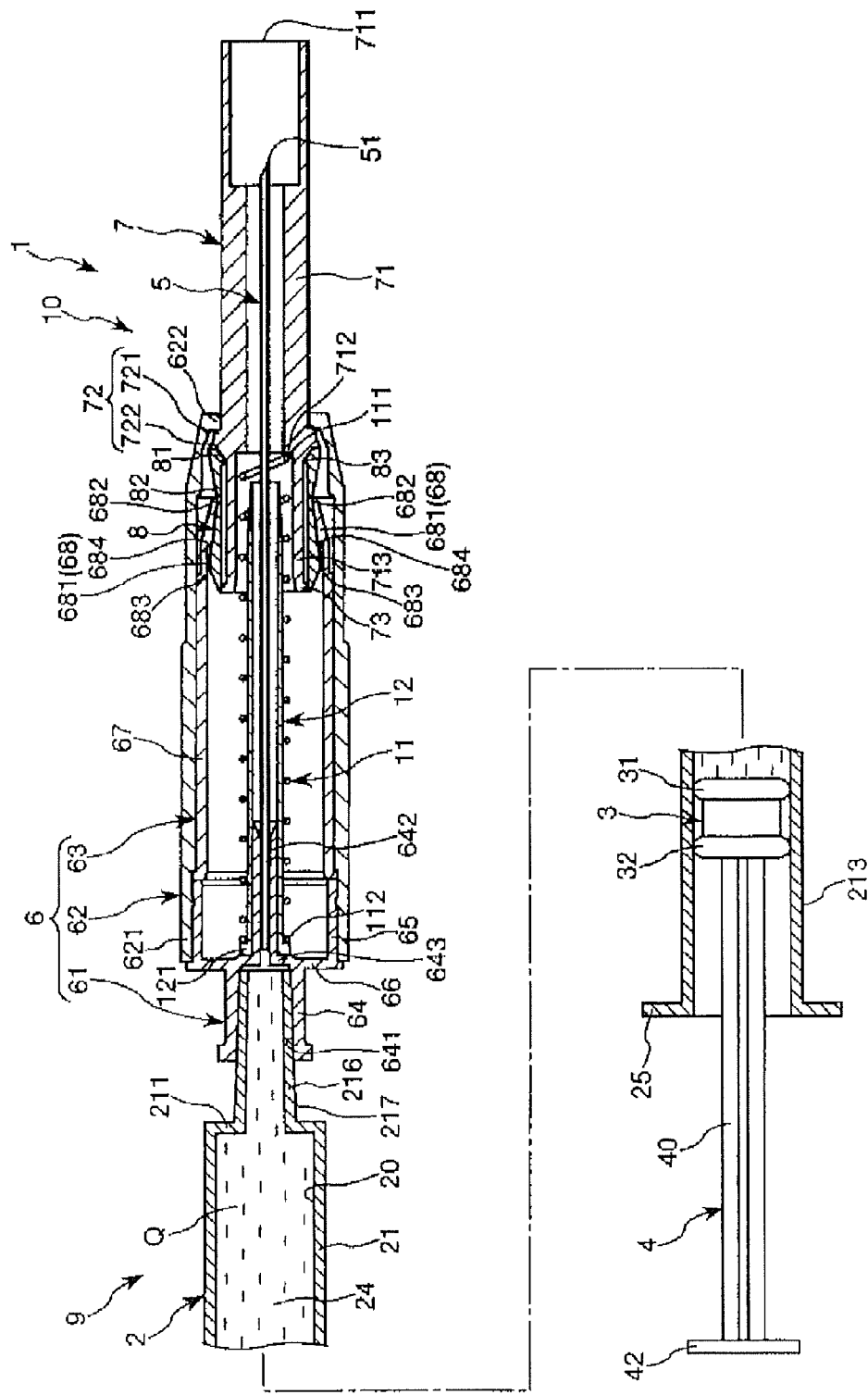
FIG. 8 is a longitudinal sectional view sequentially illustrating states during use of a second embodiment of the medicinal liquid injector (puncture needle assembly) according to the present invention.
Figure 9:
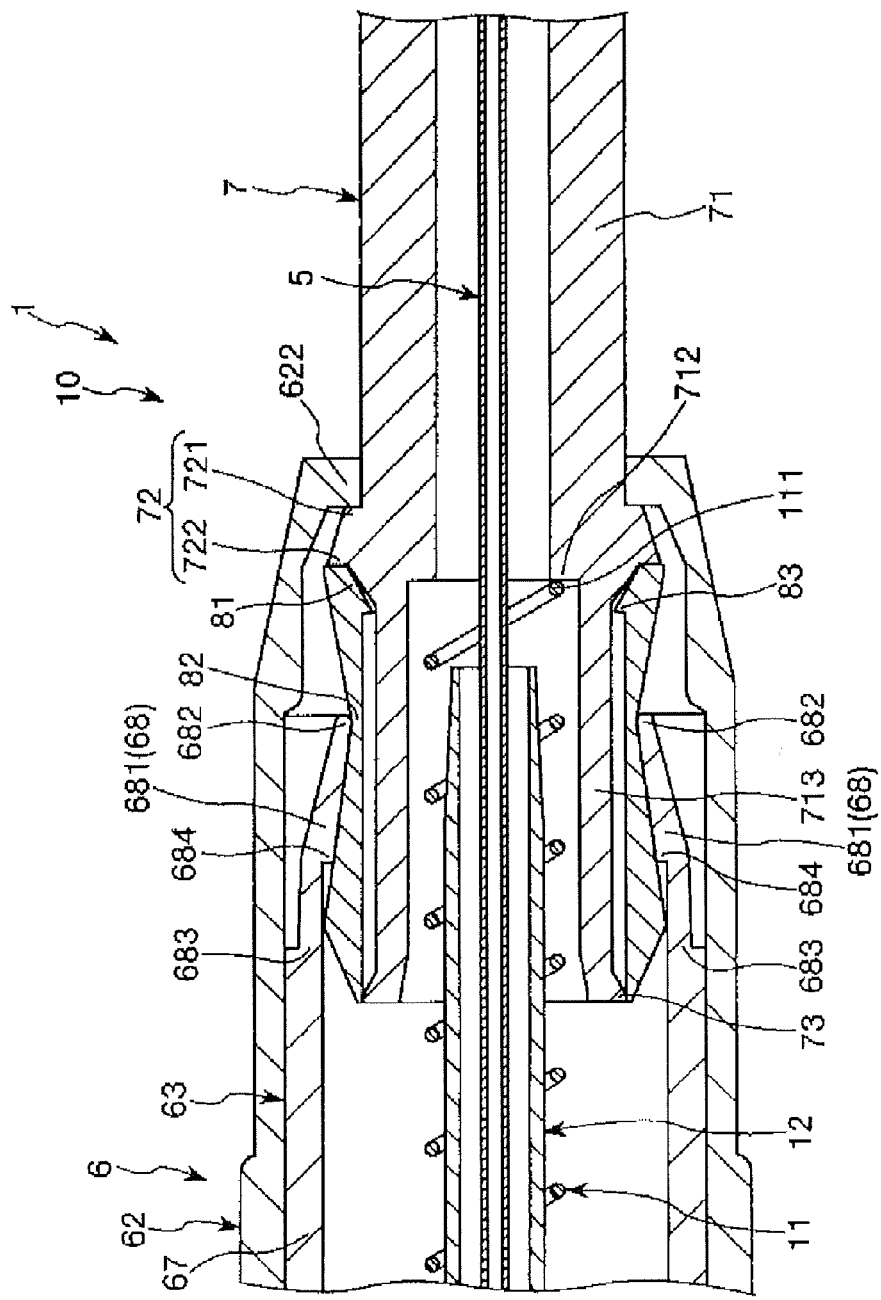
FIG. 9 is a longitudinal sectional view showing, in an enlarged form, a major part of the medicinal liquid injector shown in FIG. 8.
Figure 10:
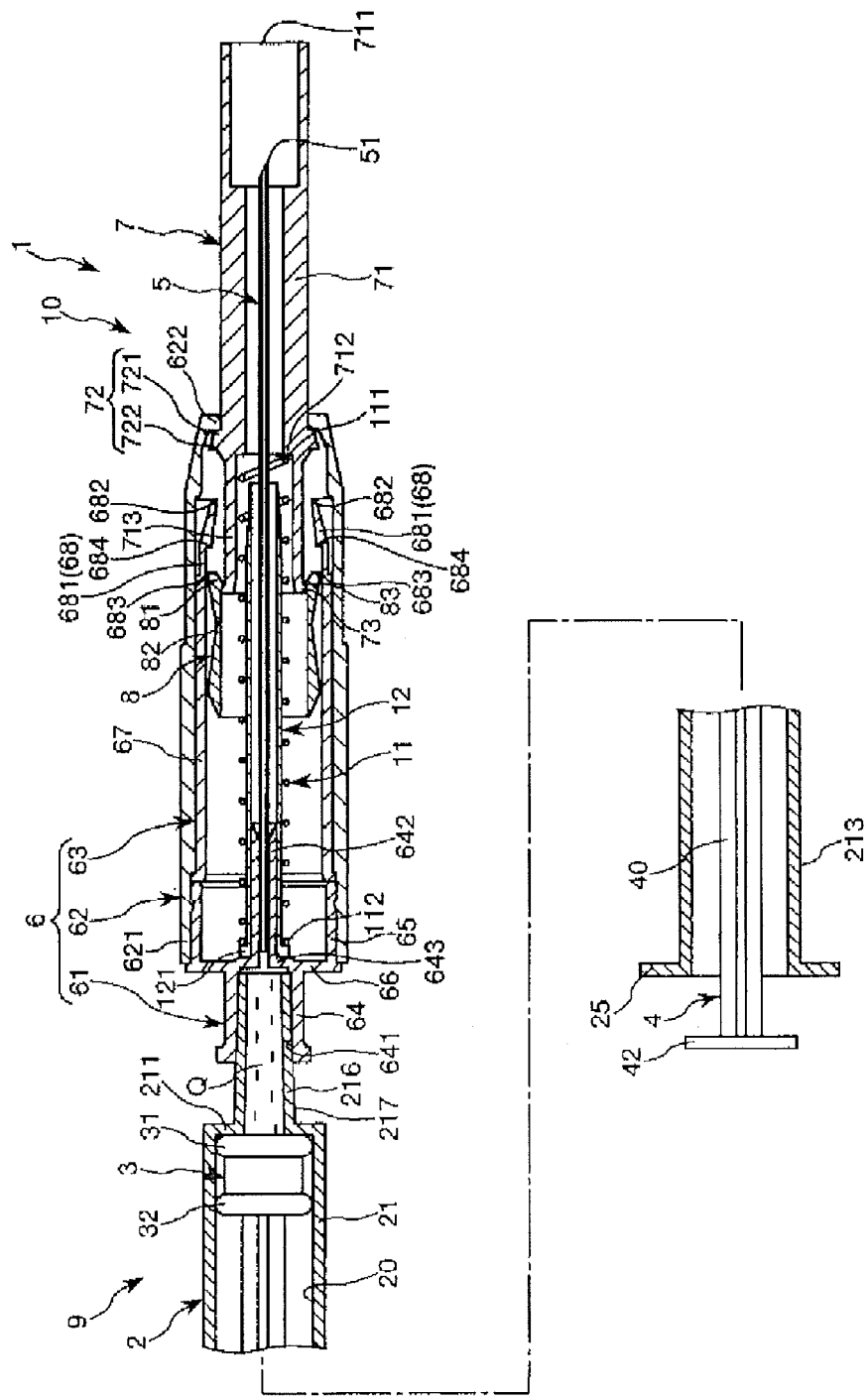
FIG. 10 is a longitudinal sectional view sequentially illustrating states during use of the medicinal liquid injector shown in FIG. 8.
Figure 11:
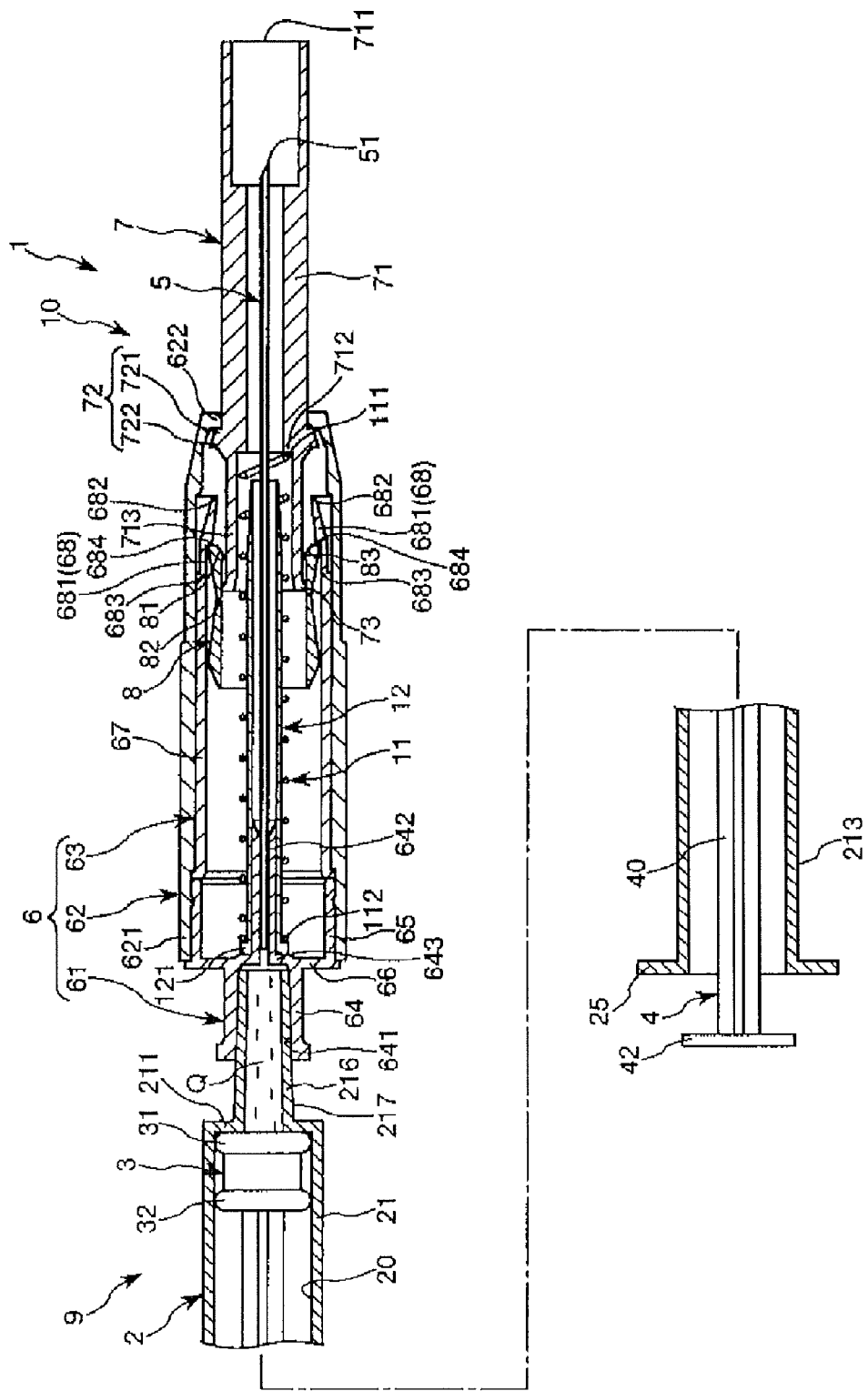
FIG. 11 is a longitudinal sectional view sequentially illustrating states during use of the medicinal liquid injector shown in FIG. 8.
Figure 12:
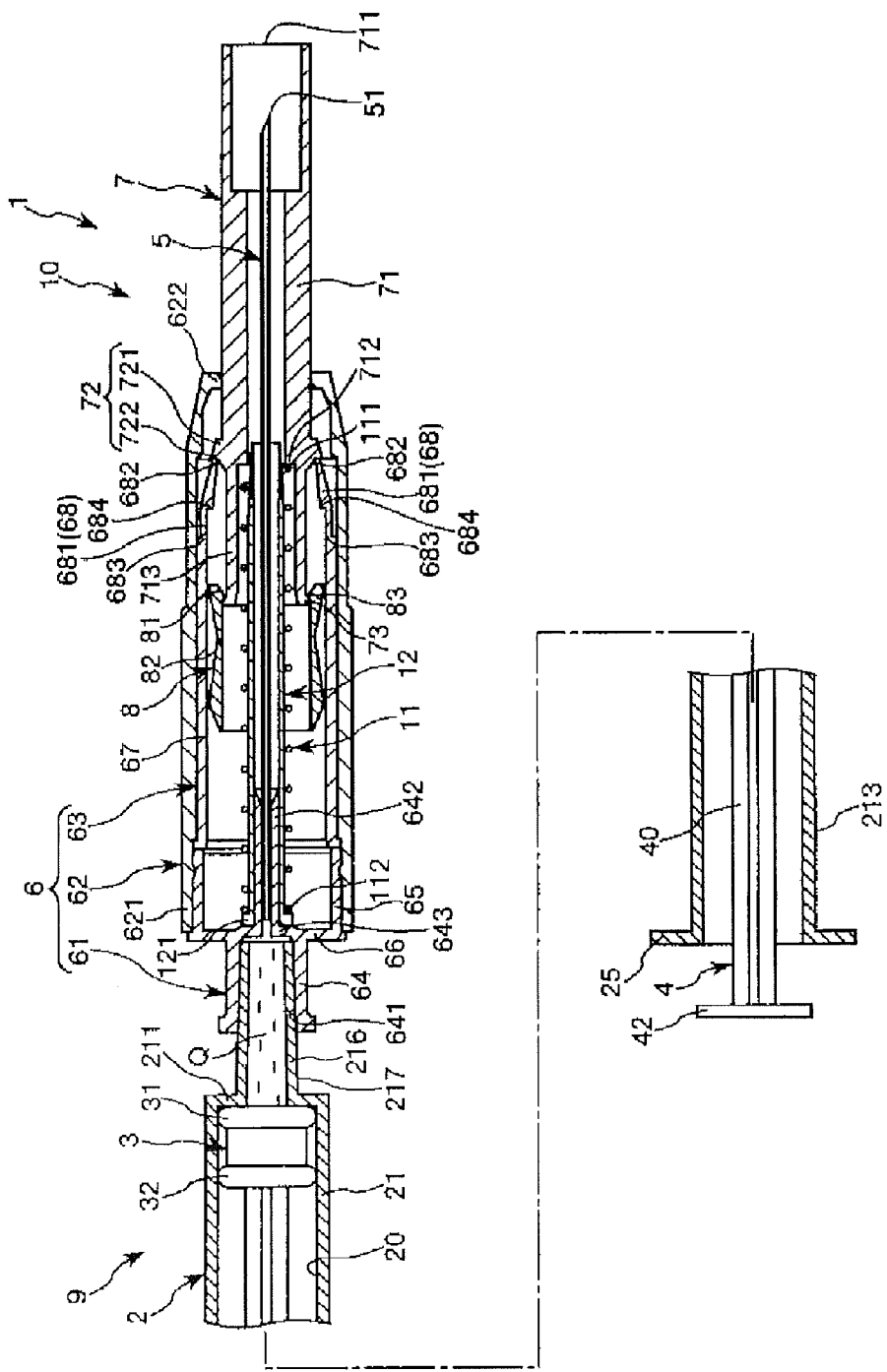
FIG. 12 is a longitudinal sectional view sequentially illustrating states during use of the medicinal liquid injector shown in FIG. 8.

FIG. 8 is a longitudinal sectional view sequentially illustrating states during use of a second embodiment of the medicinal liquid injector (puncture needle assembly) according to the present invention. FIG. 9 is a longitudinal sectional view showing, in an enlarged form, a major part of the medicinal liquid injector shown in FIG. 8. FIGS. 10 to 12 are longitudinal sectional views sequentially illustrating states during use of the medicinal liquid injector shown in FIG. 8. Incidentally, in the following explanations, for facilitating descriptions thereof, the left side in FIGS. 8 to 12 will be referred to as a "base end (proximal end)" and the right side will be referred to as a "distal end."

Next, a second embodiment of the invention will be described. Descriptions thereof will center on differences from the first embodiment described above, and descriptions of the same items will be omitted.

In a medicinal liquid injector 1 (puncture needle assembly 10) according to the second embodiment, as shown in the drawings, an engagement preventing member 8 is mounted on a base end portion 713 of a protector body 71 of a protector 7, and more specifically, to an outer peripheral portion on the base end side of an engaging section 722 of the protector body 71, in such a manner that the engagement preventing member 8 is movable relative to the protector body 71 but cannot be released therefrom.

As shown in FIGS. 8 and 9, a rib (projecting section) 83 is formed on an inner peripheral part of a distal portion 81 of the engagement preventing member 8. The rib 83 is formed so as to project toward the side of the needle tube 5 (inside) along the circumferential direction of the engagement preventing member 8 and over one circumference thereof. In other words, the rib 83 has a ring-like shape, with the center axis (axis) of the needle tube 5 being located at the center of the ring.

On the other hand, a rib (projecting section) 73, which is capable of engaging with the rib 83 of the engagement preventing member 8, is formed on an outer peripheral part of the base end (base end portion 713) of the protector body 71. The rib 73 is formed so as to project toward a side (outside) opposite to the needle tube 5 along the circumferential direction of the protector body 71 and over one circumference thereof. In other words, the rib 73 has a ring-like shape, with the center axis (axis) of the needle tube 5 being located at the center of the ring.

The ribs 73 and 83 constitute a release preventing means, which prevents the engagement preventing member 8 from becoming released from the base end portion 713 of the protector body (from the protector 7) when the protector 7 moves from the second position to the first position.

In addition, the outside diameter of an outer peripheral part of a base end portion of the engagement preventing member 8 gradually decreases from the distal end side toward the base end side. This enables the puncture needle assembly 10 to be assembled easily.

Further, each of the small pieces 681 (elastic deformable section 68) that make up the inside member 63 is inclined relative to the axis of the needle tube 5, so that a part thereof ranging from an intermediate portion to a distal portion 682 is closer to the needle tube 5 than the base portion (base end portion) 683 thereof. Each of the small pieces 681 also is provided, at an intermediate portion thereof, with a stepped part 684, with which the distal portion 81 of the engagement preventing member 8 can make contact. The stepped parts 684 of the small pieces 681 function as an assisting means for assisting assured release of the state of contact between the engagement preventing member 8 and the engaging section 722 (rib 72) when the protector 7 is moved from the second position to the first position.

When the medicinal liquid injector 1 (protector 7) is separated from a living body surface 200 after having administered a medicinal liquid Q, the protector 7 is pressed (biased) in the distal direction by a restoring force (biasing force) of a coil spring 11, so that the protector 7 moves toward and is returned to the first position, in the same manner as in the first embodiment.

However, it should be noted that in the medicinal liquid injector 1 (puncture needle assembly 10), when the protector 7 moves from the second position toward the first position (returns to the first position), at first, the engagement preventing member 8 remains at a base end portion of a body 6 due to frictional forces between the engagement preventing member 8 and an outer tube section 65 of a hub 61. In addition, only the protector 7 moves toward the first position, whereby contact between the engagement preventing member 8 and the engaging section 722 (rib 72) is released. During this course of movement, the rib 83 of the engagement preventing member 8 and the rib 73 of the protector 7 engage with each other, thereby causing the engagement preventing member 8 to move together with the protector toward the first position. More specifically, the engagement preventing member 8 is inhibited from becoming released from the base end portion 713 of the protector body 71.

In addition, the protector 7 moves from the second position to the first position in a condition where the engagement preventing member 8 is mounted on the base end portion 713 of the protector 7. Therefore, a portion on the distal end side relative to the rib 72 of the protector body 71 is supported by a rib 622 of an outside member 62, and the base end portion 713 is supported by a tubular section 67 of the inside member 63 via the engagement preventing member 8. Consequently, the protector 7 can move stably.

In this manner, as shown in FIG. 10, the protector 7 returns to the first position, whereas the engagement preventing member 8 remains on the base end side relative to the small pieces 681 (elastic deformable section 68) in a state of being mounted on the base end portion 713 of the protector body 71. This ensures that the engagement preventing function of the engagement preventing member 8 is not exhibited.

In the case that the engagement preventing member 8 moves together with the protector toward the first position, for example, in a state of making contact with the engaging section 722 of the protector 7 when the protector 7 is returned to the first position, as shown in FIG. 11, a distal portion 81 of the engagement preventing member 8 comes into contact with the stepped parts 684 of the small pieces 681. This ensures that the engagement preventing member 8 becomes stopped at that position, and only the protector 7 is capable of moving toward the first position. Then, the protector 7 returns to the first position, whereas the engagement preventing member 8 remains on the base end side relative to the small pieces 681, in a state of being mounted on the base end portion 713 of the protector body 71. Consequently, the engagement preventing function of the engagement preventing member 8 is not exhibited again.

In the case that a pressing force toward the base end side is exerted on the protector 7 starting from the condition shown in FIG. 10 or FIG. 11, the protector 7 tends to move toward the second position. However, because the engaging section 722 of the protector 7 engages with the distal portions 682 of the small pieces 681, the protector 7 is inhibited (prevented) from moving toward the side of the second position (see FIG. 12). As a result, erroneous use of a used medicinal liquid injector 1, i.e., causing the needle tube 5 to protrude to administer a medicinal liquid Q into a living body through the needle tube 5, can reliably be prevented from occurring.

Further, as mentioned previously, when the protector 7 is returned to the first position, a portion on the distal end side relative to the rib 72 of the protector body 71 is supported by the rib 622 of the outside member 62, and the base end portion 713 is supported by the tubular section 67 of the inside member 63 through the engagement preventing member 8. Consequently, chattering of the protector 7 can reliably be prevented.

Third Embodiment

Figure 13:
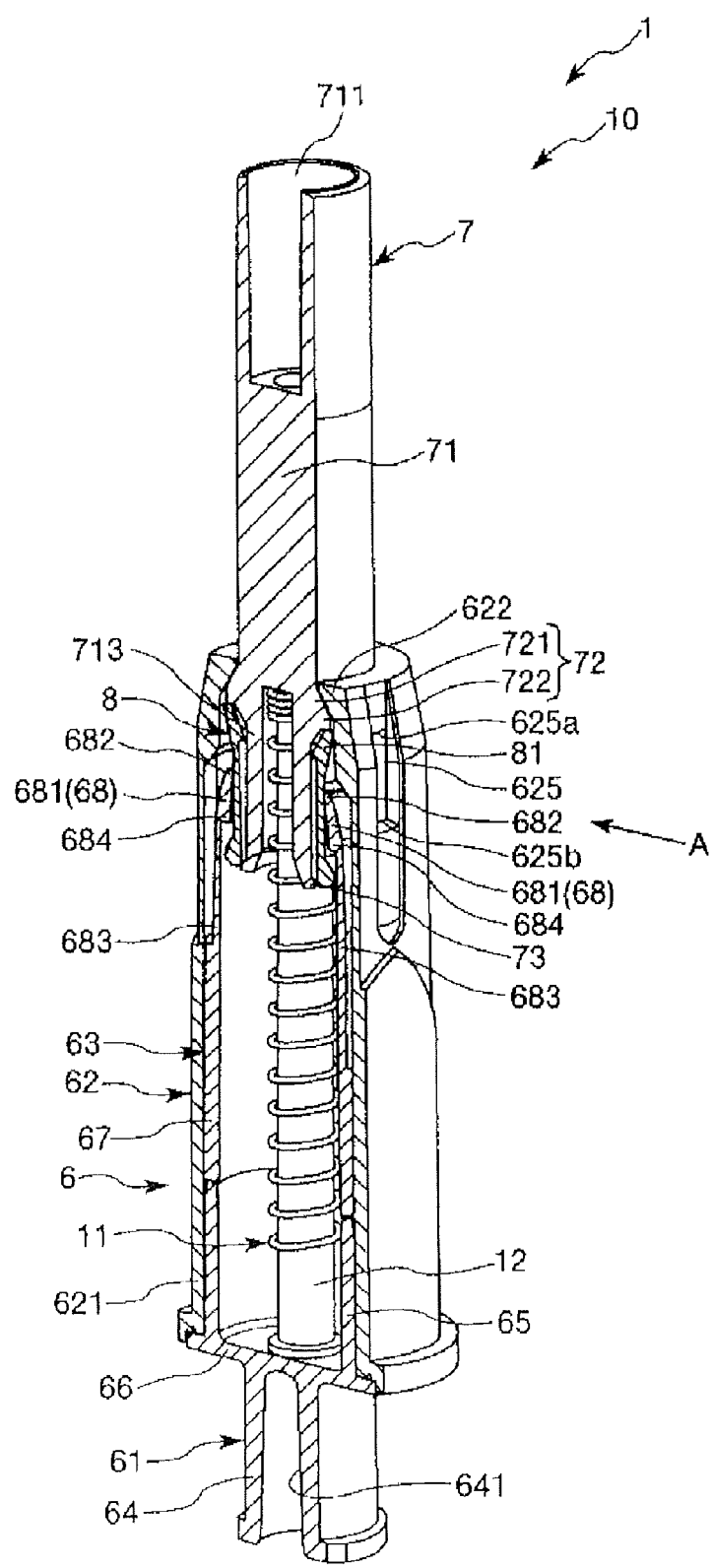
FIG. 13 is a longitudinal sectional perspective view showing an unused state of a third embodiment of the medicinal liquid injector (puncture needle assembly) according to the present invention.
Figure 14:
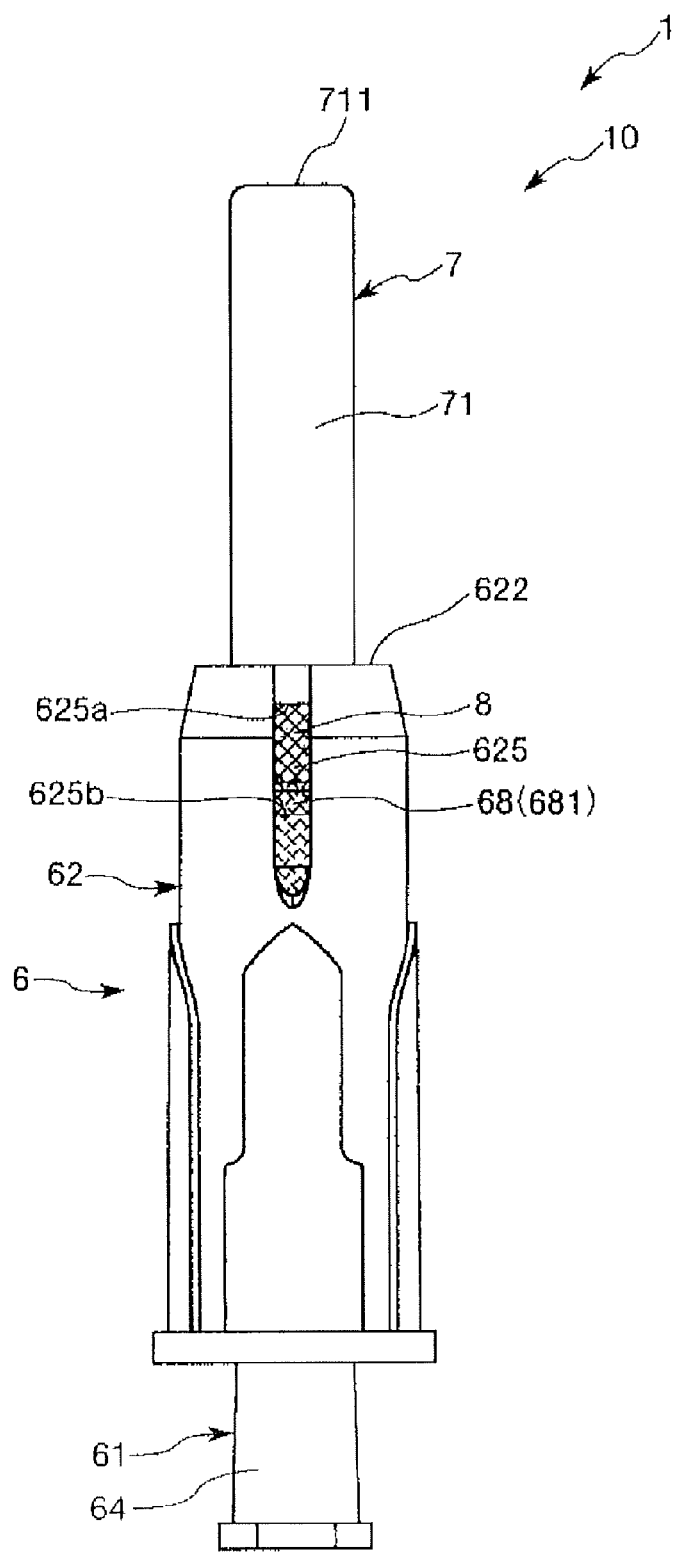
FIG. 14 is a view (side view) of the medicinal liquid injector shown in FIG. 13, as viewed along a direction of the arrow A.
Figure 15:
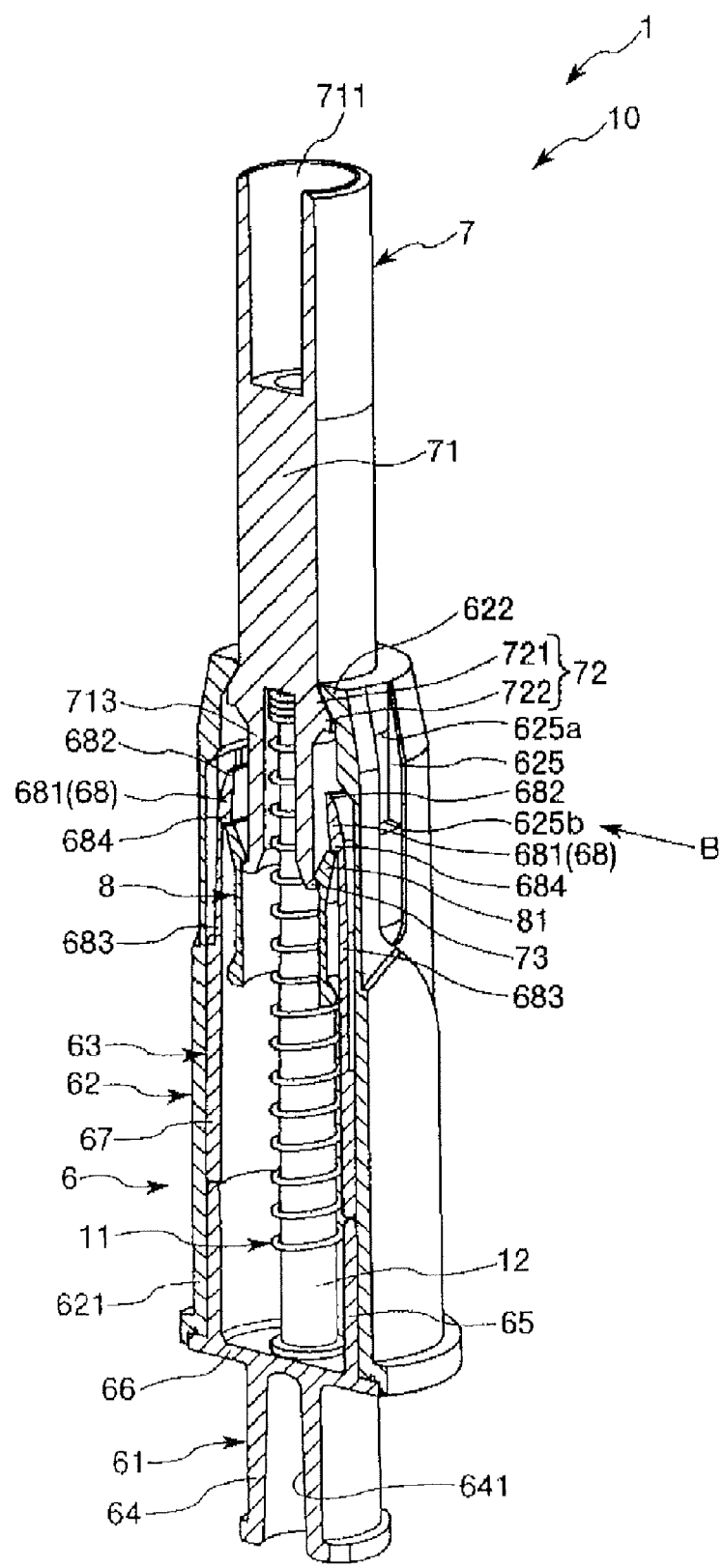
FIG. 15 is a longitudinal sectional perspective view showing a used state of the third embodiment of the medicinal liquid injector (puncture needle assembly) according to the present invention.
Figure 16:
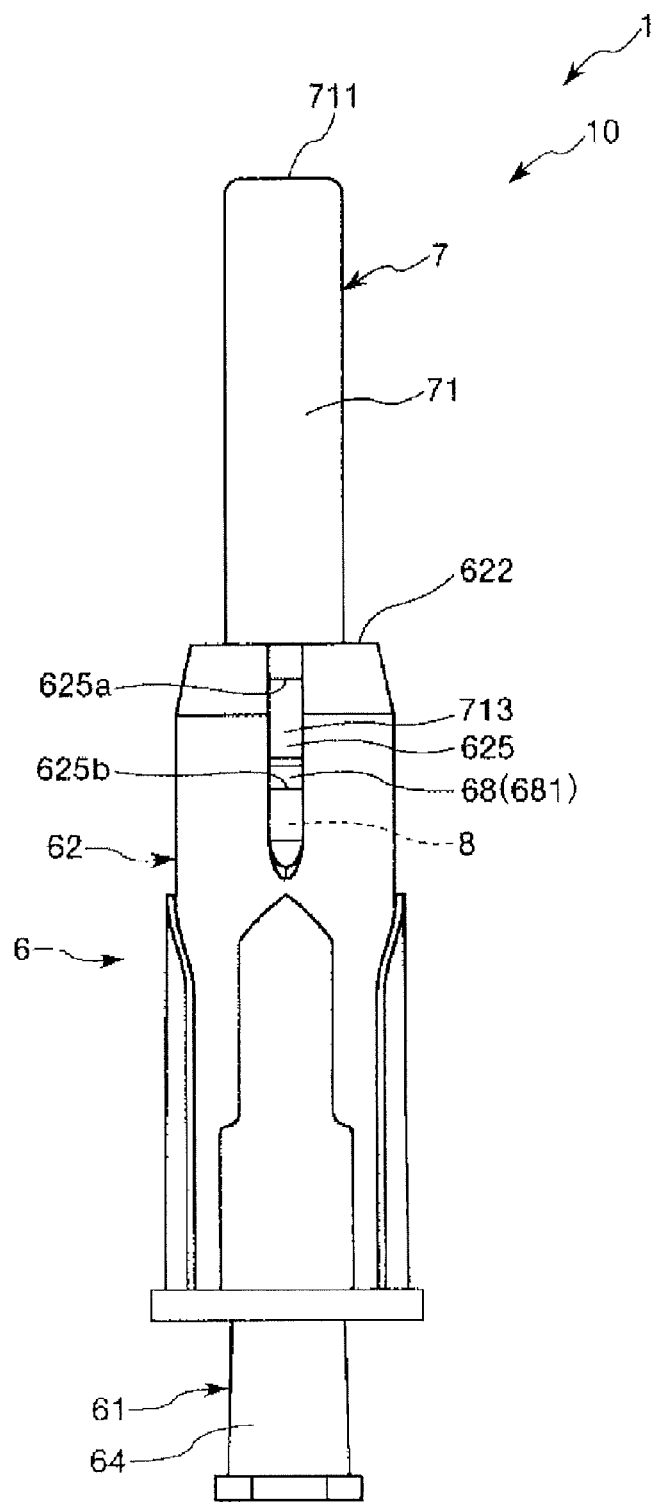
FIG. 16 is a view (side view) of the medicinal liquid injector shown in FIG. 15, as viewed along a direction of the arrow B.

FIG. 13 is a longitudinal sectional perspective view showing an unused state of a third embodiment of the medicinal liquid injector (puncture needle assembly) according to the present invention. FIG. 14 is a view (side view) of the medicinal liquid injector shown in FIG. 13, as viewed in a direction along the arrow A. FIG. 15 is a longitudinal sectional perspective view showing a used state of the third embodiment of the medicinal liquid injector (puncture needle assembly) according to the present invention. FIG. 16 is a view (side view) of the medicinal liquid injector shown in FIG. 15, as viewed in a direction along the arrow B. Incidentally, in the following explanations, for facilitating descriptions thereof, the upper side in FIGS. 13 to 16 will be referred to as a "distal end" and the lower side will be referred to as a "base end (proximal end)."

Next, referring to these figures, a third embodiment of the puncture needle assembly and the medicinal liquid injector according to the present invention will be described below. The following descriptions shall center on differences from the above-described embodiments, and descriptions of the same items will be omitted.

This embodiment is the same as the above-described second embodiment, except for differences in the configuration of the outside member of the body.

In the puncture needle assembly 10 shown in FIGS. 13 to 16, an outside member 62 of a body 6 is provided, at positions on opposite sides of the axis thereof, with windows (through-holes) 625, which penetrate through a wall section (tubular wall) in the thickness direction of the wall section. Although at least one window 625 is sufficient, in the present embodiment, two windows 625 are provided. Each of the windows 625 has an elongate shape, which is oriented lengthwise along the longitudinal direction of the body 6. In the present embodiment, with reference to the longitudinal direction, the window 625 is formed such that a distal end 625*a* thereof is located at the same position as the distal end of an engagement preventing member 8, and a proximal end 625*b* thereof is located at the same position as a stepped part 684 of each of the small pieces 681.

Incidentally, the distal end 625*a* and the proximal end 625*b* may be located on the base end (proximal) side relative to the above-mentioned positions, respectively. For instance, when the proximal end 625*b* is located on the proximal side relative to the position of the stepped part 684 of each of the small pieces 681, it is preferable to provide the window 625 having a mark thereon at the same position as the stepped part 684 of the small piece 681.

In addition, the small pieces 681 preferably are transparent and different in color from the engagement preventing member 8 of the protector 7. In the present embodiment, the protector 7 is white in color, whereas the engagement preventing member 8 is green. Also, an inside member 63 as a whole inclusive of the small pieces 681 is transparent. Incidentally, in FIG. 14, the engagement preventing member 8 is indicated by half-tone meshed hatching (cross hatching).

In the puncture needle assembly 10 shown in FIG. 14 (in FIG. 13 as well), which is in an unused state, the green-colored engagement preventing member 8, which is mounted on the protector 7, can visually be confirmed through the windows 625 (i.e., in areas of the small pieces 681, through the transparent small pieces 681 in a see-through manner). Consequently, it can be confirmed that the puncture needle assembly 10 is in an unused state.

In the puncture needle assembly 10 shown in FIG. 15, which has been placed in a used state as a result of being used in the same manner as the puncture needle assembly 10 of the aforementioned second embodiment, the position of the engagement preventing member 8 relative to the protector 7 has been shifted, whereby a distal portion 81 of the engagement preventing member 8 comes into contact with the stepped parts 684 of the small pieces 681. In this condition, as shown in FIG. 16, the white color of the protector 7 (base end portion 713) can be confirmed visually through each of the windows 625. As a result, it can be confirmed that the puncture needle assembly 10 is in a used state.

With such a configuration, the color (member), which is visible through each of the windows 625, can be confirmed. Therefore, whether the puncture needle assembly 10 is in an unused or a used state can securely be discriminated.

Incidentally, the windows 625 are not limited to parts composed of through-holes formed in the outside member 62. For example, each of the windows 625 may be formed as a transparent portion in the outside member 62.

While the puncture needle assembly and the medicinal liquid injector according to the present invention have been described above with reference to the embodiments shown in the drawings, the invention is not limited to the embodiments. Parts constituting the puncture needle assembly and the medicinal liquid injector can be replaced by other parts of arbitrary configurations, which are capable of exhibiting functions identical or similar to the functions of the original parts. Further, arbitrary structures may be added.

In addition, the present invention may involve a combination of any arbitrary two or more configurations (features) of the embodiments described above.

Further, in the present invention, the puncture needle assembly is not limited to being used as an injection needle. For example, the puncture needle assembly can also be used as a blood drawing needle.

Industrial Applicability

The puncture needle assembly according to the present invention includes a needle tube having a sharp needle point at a distal end thereof, a body including a tubular body section in which the needle tube is partially inserted, a hub to which a base end portion of the needle tube is fixed and which is provided at a base end portion of the tubular body section, and an elastic deformable section provided on a distal end side relative to the base end portion of the tubular body section, a protector supported on the body so as to be capable of moving along an axial direction of the needle tube between a first position at which the protector covers at least the needle point of the needle tube, and a second position at which the needle point is exposed and which is on a base end side relative to the first position, the protector having an engaging section engaging with the elastic deformable section when the protector is in the first position, an engagement preventing member which, when the protector moves from the first position to the second position, makes contact with the engaging section to exhibit an engagement preventing function, and which permits the engaging section to move past the elastic deformable section without engaging with the elastic deformable section, and biasing means biasing the protector in a direction from the second position toward the first position. The protector is biased by a biasing force of the biasing means to move to the first position when the protector is pushed to move from the first position to the second position against the biasing force of the biasing means and then pushing thereof is released. Thereafter, when it is attempted to move the protector in the first position toward the second position, the engagement preventing function of the engagement preventing member is not exhibited and the engaging section engages with the elastic deformable section, thereby preventing the protector from moving toward the second position side. Therefore, the needle point of the needle tube can securely be prevented from becoming exposed unintentionally from the protector. Accordingly, the puncture needle assembly according to the present invention has industrial applicability.

The invention claimed is:

1. A puncture needle assembly comprising:
a needle tube having a sharp needle point at a distal end thereof;
a body including a tubular body section in which the needle tube is partially inserted, a hub to which a base end portion of the needle tube is fixed and which is provided at a base end portion of the tubular body section, and an elastic deformable section provided on a distal end side relative to the base end portion of the tubular body section;
a protector supported on the body so as to be capable of moving along an axial direction of the needle tube between a first position at which the protector covers at least the needle point of the needle tube, and a second position at which the needle point is exposed and which is on a base end side relative to the first position, the protector having an engaging section engaging with the elastic deformable section when the protector is in the first position;
an engagement preventing member which, when the protector moves from the first position to the second position, makes contact with the engaging section to exhibit an engagement preventing function, and which permits the engaging section to move past the elastic deformable section without engaging with the elastic deformable section; and
biasing means biasing the protector in a direction from the second position toward the first position,
wherein the protector is biased by a biasing force of the biasing means to move to the first position when the protector is pushed to move from the first position to the second position against the biasing force of the biasing means and then pushing thereof is released, and when it is attempted to thereafter move the protector in the first position toward the second position, the engagement preventing function of the engagement preventing member is not exhibited and the engaging section engages with the elastic deformable section, thereby preventing the protector from moving toward the second position side,
wherein the engagement preventing member is mounted on the protector, and when the protector moves from the first position to the second position, the engagement preventing member moves together with the protector so as to move past the elastic deformable section, and
wherein when the protector is in the first position, a distal portion of the elastic deformable section is located at an intermediate portion of the engagement preventing member, in a condition where the engagement preventing member is mounted on the protector.

2. The puncture needle assembly according to claim 1, wherein the protector is tubular in overall shape, and the engaging section is composed of a projecting section formed at an outer peripheral portion of the protector, and
the engagement preventing member is tubular in overall shape and is mounted on an outer peripheral portion on the base end side of the engaging section of the protector.

3. The puncture needle assembly according to claim 1, wherein when the protector is in the first position, the elastic deformable section is located on an outer peripheral side of the engagement preventing member, in a condition where the engagement preventing member is mounted on the protector, and
when the protector moves from the first position to the second position, the engagement preventing member is capable of moving together with the protector and pressing the elastic deformable section outwardly so as to elastically deform the elastic deformable section.

4. The puncture needle assembly according to claim 1, wherein the engagement preventing member is mounted on the protector upon return of the protector from the second position to the first position.

5. The puncture needle assembly according to claim 1, further comprising release preventing means for preventing the engagement preventing member from becoming released from the protector when the protector moves from the second position to the first position.

6. The puncture needle assembly according to claim 1, further comprising assisting means for assisting assured release of a contact state of the engagement preventing member with the engaging section when the protector moves from the second position to the first position.

7. The puncture needle assembly according to claim 1, wherein the engagement preventing member becomes released from the protector when the protector moves from the second position to the first position.

8. The puncture needle assembly according to claim 1, wherein when the protector moves from the second position to the first position, a contact state of the engagement preventing member with the engaging section becomes released, so that the engagement preventing function is not exhibited before movement of the engaging section past the elastic deformable section.

9. The puncture needle assembly according to claim 1, wherein when the protector moves from the second position to the first position, the engagement preventing member remains on the base end side relative to the elastic deformable section so that the engagement preventing function is not exhibited.

10. The puncture needle assembly according to claim 1, wherein when the protector is in the first position, the elastic deformable section is in a natural state with no external forces exerted thereon.

11. The puncture needle assembly according to claim 1, wherein whether the puncture needle assembly is unused or used can be distinguished.

12. A medicinal liquid injector comprising:
the puncture needle assembly according to claim 1; and
a container having a mounting section on which the hub of the puncture needle assembly is mounted, and which is preliminarily filled with a medicinal liquid.

13. A puncture needle assembly comprising:
a needle tube having a sharp needle point at a distal end thereof;
a body including a tubular body section in which the needle tube is partially inserted, a hub to which a base end portion of the needle tube is fixed and which is provided at a base end portion of the tubular body section, and an elastic deformable section provided on a distal end side relative to the base end portion of the tubular body section;
a protector supported on the body so as to be capable of moving along an axial direction of the needle tube between a first position at which the protector covers at least the needle point of the needle tube, and a second position at which the needle point is exposed and which is on a base end side relative to the first position, the protector having an engaging section engaging with the elastic deformable section when the protector is in the first position;
an engagement preventing member which, when the protector moves from the first position to the second position, makes contact with the engaging section to exhibit an engagement preventing function, and which permits the engaging section to move past the elastic deformable section without engaging with the elastic deformable section; and
biasing means biasing the protector in a direction from the second position toward the first position,
wherein the protector is biased by a biasing force of the biasing means to move to the first position when the protector is pushed to move from the first position to the second position against the biasing force of the biasing means and then pushing thereof is released, and when it is attempted to thereafter move the protector in the first position toward the second position, the engagement preventing function of the engagement preventing member is not exhibited and the engaging section engages with the elastic deformable section, thereby preventing the protector from moving toward the second position side, and
wherein the engagement preventing member is mounted on the protector upon return of the protector from the second position to the first position, and when the protector moves from the first position to the second position, the engagement preventing member moves together with the protector so as to move past the elastic deformable section.

14. The puncture needle assembly according to claim 13, wherein the protector is tubular in overall shape, and the engaging section is composed of a projecting section formed at an outer peripheral portion of the protector, and the engagement preventing member is tubular in overall shape and is mounted on an outer peripheral portion on the base end side of the engaging section of the protector.

15. The puncture needle assembly according to claim 13, wherein when the protector is in the first position, the elastic deformable section is located on an outer peripheral side of the engagement preventing member, in a condition where the engagement preventing member is mounted on the protector, and
when the protector moves from the first position to the second position, the engagement preventing member is capable of moving together with the protector and pressing the elastic deformable section outwardly so as to elastically deform the elastic deformable section.

16. The puncture needle assembly according to claim 13, further comprising release preventing means for preventing the engagement preventing member from becoming released from the protector when the protector moves from the second position to the first position.

17. The puncture needle assembly according to claim 13, further comprising assisting means for assisting assured release of a contact state of the engagement preventing member with the engaging section when the protector moves from the second position to the first position.

18. The puncture needle assembly according to claim 13, wherein when the protector moves from the second position to the first position, a contact state of the engagement preventing member with the engaging section becomes released, so that the engagement preventing function is not exhibited before movement of the engaging section past the elastic deformable section.

19. The puncture needle assembly according to claim 13, wherein when the protector moves from the second position to the first position, the engagement preventing member remains on the base end side relative to the elastic deformable section so that the engagement preventing function is not exhibited.

20. The puncture needle assembly according to claim 13, wherein when the protector is in the first position, the elastic deformable section is in a natural state with no external forces exerted thereon.

21. The puncture needle assembly according to claim 13, wherein whether the puncture needle assembly is unused or used can be distinguished.

22. A medicinal liquid injector comprising:
the puncture needle assembly according to claim 13; and
a container having a mounting section on which the hub of the puncture needle assembly is mounted, and which is preliminarily filled with a medicinal liquid.

23. A puncture needle assembly comprising:
a needle tube having a sharp needle point at a distal end thereof;
a body including a tubular body section in which the needle tube is partially inserted, a hub to which a base end portion of the needle tube is fixed and which is provided at a base end portion of the tubular body section, and an elastic deformable section provided on a distal end side relative to the base end portion of the tubular body section;
a protector supported on the body so as to be capable of moving along an axial direction of the needle tube between a first position at which the protector covers at least the needle point of the needle tube, and a second position at which the needle point is exposed and which is on a base end side relative to the first position, the protector having an engaging section engaging with the elastic deformable section when the protector is in the first position;

an engagement preventing member which, when the protector moves from the first position to the second position, makes contact with the engaging section to exhibit an engagement preventing function, and which permits the engaging section to move past the elastic deformable section without engaging with the elastic deformable section; and biasing means biasing the protector in a direction from the second position toward the first position, wherein the protector is biased by a biasing force of the biasing means to move to the first position when the protector is pushed to move from the first position to the second position against the biasing force of the biasing means and then pushing thereof is released, and when it is attempted to thereafter move the protector in the first position toward the second position, the engagement preventing function of the engagement preventing member is not exhibited and the engaging section engages with the elastic deformable section, thereby preventing the protector from moving toward the second position side, wherein the engagement preventing member is mounted on the protector, and when the protector moves from the first position to the second position, the engagement preventing member moves together with the protector so as to move past the elastic deformable section, and wherein the puncture needle assembly further comprises release preventing means for preventing the engagement preventing member from becoming released from the protector when the protector moves from the second position to the first position.

24. The puncture needle assembly according to claim 23, wherein the protector is tubular in overall shape, and the engaging section is composed of a projecting section formed at an outer peripheral portion of the protector, and the engagement preventing member is tubular in overall shape and is mounted on an outer peripheral portion on the base end side of the engaging section of the protector.

25. The puncture needle assembly according to claim 23, wherein when the protector is in the first position, the elastic deformable section is located on an outer peripheral side of the engagement preventing member, in a condition where the engagement preventing member is mounted on the protector, and when the protector moves from the first position to the second position, the engagement preventing member is capable of moving together with the protector and pressing the elastic deformable section outwardly so as to elastically deform the elastic deformable section.

26. The puncture needle assembly according to claim 23, further comprising assisting means for assisting assured release of a contact state of the engagement preventing member with the engaging section when the protector moves from the second position to the first position.

27. The puncture needle assembly according to claim 23, wherein when the protector moves from the second position to the first position, a contact state of the engagement preventing member with the engaging section becomes released, so that the engagement preventing function is not exhibited before movement of the engaging section past the elastic deformable section.

28. The puncture needle assembly according to claim 23, wherein when the protector moves from the second position to the first position, the engagement preventing member remains on the base end side relative to the elastic deformable section so that the engagement preventing function is not exhibited.

29. The puncture needle assembly according to claim 23, wherein when the protector is in the first position, the elastic deformable section is in a natural state with no external forces exerted thereon.

30. The puncture needle assembly according to claim 23, wherein whether the puncture needle assembly is unused or used can be distinguished.

31. A medicinal liquid injector comprising:
the puncture needle assembly according to claim 23; and
a container having a mounting section on which the hub of the puncture needle assembly is mounted, and which is preliminarily filled with a medicinal liquid.

* * * * *